US007554009B2

(12) United States Patent
Davies et al.

(10) Patent No.: US 7,554,009 B2
(45) Date of Patent: Jun. 30, 2009

(54) GENERATION OF PLANTS WITH ALTERED OIL CONTENT

(75) Inventors: John Davies, Portland, OR (US); Sandra Peters, Portland, OR (US); Hein Tsoeng Ng, Beaverton, OR (US)

(73) Assignee: Agrinomics, LLC, Portland, OR (US)

( * ) Notice: Subject to any disclaimer, the term of this patent is extended or adjusted under 35 U.S.C. 154(b) by 98 days.

(21) Appl. No.: 11/596,833

(22) PCT Filed: May 26, 2005

(86) PCT No.: PCT/US2005/018919

§ 371 (c)(1),
(2), (4) Date: Nov. 17, 2006

(87) PCT Pub. No.: WO2005/118822

PCT Pub. Date: Dec. 15, 2005

(65) Prior Publication Data

US 2007/0250960 A1  Oct. 25, 2007

Related U.S. Application Data

(60) Provisional application No. 60/575,202, filed on May 28, 2004.

(51) Int. Cl.
*A01H 5/00* (2006.01)
*C12N 15/82* (2006.01)
(52) U.S. Cl. ........................ 800/298; 800/281
(58) Field of Classification Search ............ None
See application file for complete search history.

(56) References Cited

U.S. PATENT DOCUMENTS

| 5,639,790 | A | 6/1997 | Voelker et al. |
| 5,704,160 | A | 1/1998 | Bergquist et al. |
| 6,229,033 | B1 | 5/2001 | Knowlton |
| 6,248,939 | B1 | 6/2001 | Leto et al. |
| 2002/0023281 | A1 | 2/2002 | Gorlach et al. |

FOREIGN PATENT DOCUMENTS

| EP | 1 033 405 | | 9/2000 |
| EP | 1033405 | A2 * | 9/2000 |
| WO | WO99/58654 | | 11/1999 |
| WO | WO01/83697 | | 11/2001 |
| WO | WO03/079766 | | 10/2003 |

OTHER PUBLICATIONS

Zou et al. (The Plant Cell, 9:909-923, 1997).*
Jako et al. (Plant Physiol. 126:861-874, 2001).*
Keskin et al. (Protein Science, 13:1043-1055, 2004.*
Thornton et al. (Nature structural Biology, structural genomics supplement, Nov. 2000).*
Guo et al. (PNAS, 101: 9205-9210, 2004).*
Wells, (Biochemistry 29:8509-8517, 1990).*
Ngo et al., (The Protein Folding Problem and Tertiary Structure Prediction, K. Merz., and S. Le Grand (eds.) pp. 492-495, 1994).*
Doerks et al., (TIG, 14:248-250, 1998).*
Smith et al. (Nature Biotechnology, 15:1222-1223, 1997).*
Bork et al. (TIG, 12:425-427, 1996).*
Broun et al. (Science, 282:1315-1317, 1998).*
Anoop et al., "Modulation of citrate metabolism alters aluminum tolerance in yeast and transgenic canola overexpressing a mitochondrial citrate synthase," *Plant Physiol.*, 132:2205-2217, 2003.
Beisson et al., "Arabidopsis genes involved in acyl lipid metabolism. A 2003 census of the candidates, a study of the distribution of expressed sequence tags in organs, and a web-based database," *Plant Physiol.*, 132:681-697, 2003.
Bert et al., "Comparative genetic analysis of quantitative traits in sunflower (*Helianthus annus* L.). 2. Chracterisation of QTL involved in developmental and agronomic traits," *Theor. Appl. Genet.*, 107:181-189, 2003.
Colbert et al., "High-throughput screening for induced point mutations," *Plant Physiol.*, 126(2):480-484, 2001.
Dehesh et al., "Overexpression of 3-ketoacyl-acyl-carrier protein synthase IIIs in plants reduces the rate of lipid synthesis," *Plant Physiol.*, 125:1103-1114, 2001.
Eastmond and Graham, "Re-examining the role glyoxylate cycle in oilseeds," *Trends Plant Sci.*, 6(2):72-77, 2001.
Eccleston and Ohlrogge, "Expressions of lauroyl-acyl carrier protein thioesterase in *brassica napus* seeds induces pathways for both fatty acid oxidation and biosynthesis and implies a set point for triacylglycerol accumulation," *Plant Cell.* 10:613-621, 1998.
Fatland et al., "Molecular biology of cytosolic acetyl-CoA generation," *Biochem. Soc. Trans.*, 28(6):593-595, 2000.
Fatland et al., "Reverse genetic characterization of cytosolic acetyl-CoA generation by ATP-citrate lyase in Arabidopsis," *Plant Cell*, 17:182-203, 2005.
Feldmann et al., "A Dwarf Mutant of Arabidopsis Generated by T-DNA Insertion Mutagenesis," *Science*, 243(4896):1351-1354, 1989.
Focks and Benning, "*wrinkled1*: A novel, low-seed-oil mutant of Arabidopsis with a deficiency in the seed-specific regulation of carbohydrate metabolism," *Plant Physiol.*, 118:91-101, 1998.
Girke et al., "Microarray analysis of developing Arabidopsis seeds," *Plant Physiol.*, 124:1570-1581, 2000.
Jako et al., "Seed-specific over-expression of an Arabidopsis cDNA encoding a diacylglycerol acyltransferase enhances seed oil content and seed weight," *Plant Physiol.*, 126(2):861-874, 2001.
James and Dooner, "Isolation of EMS-induced mutants in Arabidopsis altered in seed fatty acid composition," *Theor. Appl. Genet.*, 80(2):241-245, 1990.
Katavic et al., "Alteration of seed fatty acid composition by an ethyl methanesulfonate-induced mutation in Arabidopsis thaliana affecting diacylglycerol acyltransferase activity," *Plant Physiol.*, 108:399-409, 1995.

(Continued)

*Primary Examiner*—Elizabeth F McElwain
(74) *Attorney, Agent, or Firm*—Klarquist Sparkman, LLP

(57) ABSTRACT

The present invention is directed to plants that display an altered oil content phenotype due to altered expression of a HIO1002 nucleic acid. The invention is further directed to methods of generating plants with an altered oil content phenotype.

9 Claims, No Drawings

OTHER PUBLICATIONS

Katavic et al., "Utility of the *Arabidopsis FAE1* and yeast *SLC-1* genes for improvements in erucic acid and oil content in rapeseed," *Biochem Soc. Trans.*, 28(6):935-937, 2000.

Larson et al., "Acyl CoA profiles of trangenic plants that accumulate medium-chain fatty acids indicate inefficient storage lipid synthesis in developing oilseeds," *Plant J.*, 32:519-527, 2002.

Lemieux et al., "Mutants of Arabidopsis with alterations in seed lipid fatty acid composition," *Theor. Appl. Genet.*, 80(2):234-240, 1990.

Lin et al., "The Pex 16p homolog SSE1 and storage organelle formation in *Arabidopsis* seeds," *Science*. 284:328-330, 1999.

Lionneton et al., "Development of an AFLP-based linkage map and localization of QTLs for seed fatty acid content in condiment mustard (*Brassica juncea*)," *Genome*, 45(6):1203-1215, 2002.

Liu and Butow, "A transcriptional switch in the expression of yeast tricarboxylic acid cycle genes in response to a reduction or loss of respiratory function," *Mol. Cell. Biol.*, 19:6720-6728, 1999.

McCallum et al., "Targeted screening for induced mutations," *Nat. Biotechnol.*, 18(4):455-457, 2000.

Mekhedov et al., "Toward a functional catalog of the plant genome. A survey of genes for lipid biosynthesis," *Plant Physiol.*, 122:389-401, 2000.

Moire et al., "Impact of unusual fatty acid synthesis on futile cycling through β-oxidation and on gene expression in transgenic plants," *Plant Physiol.*, 134:432-442, 2004.

Neuhaus and Emes, "Nonphotosynthetic Metabolism In Plastids," *Annu. Rev. Plant Physio. Plant Mol. Biol.*, 51:111-140, 2000.

O'Hara et al., "Fatty acid and lipid biosynthetic genes are expressed at constant molar ratios but different absolute levels during embryogenesis," *Plant Physiol.*, 129:310-320, 2002.

Okuley et al., "Arabidopsis FAD2 Gene Encodes the Enzyme That Is Essential for Polyunsaturated Lipid Synthesis," *Plant Cell*, 6:147-158, 1994.

Pritchard et al., "Germination and storage reserve mobilization are regulated independently in *Arabidopsis*," *Plant J.*, 31(5):639-647, 2002.

Rangasamy and Ratledge, "Compartmentation of ATP:Citrate lyase in plants," *Plant Physiol.*, 122:1225-1230, 2000.

Rangasamy and Ratledge, "Genetic enhancement of fatty acid synthesis by targeting rat liver ATP:citrate lyase into plastids of tobacco," *Plant Physiol.*, 122:1231-1238, 2000.

Ratledge et al, "Correlation of ATP/citrate lyase activity with lipid accumulation in developing seeds of *Brassica napus* L.," *Lipids*, 32(1):7-12, 1997.

Rawsthorne, S., "Carbon flux and fatty acid synthesis in plants," *Prog Lipid Res.*, 41:182-196, 2002.

Ruuska et al., "Contrapuntal networks of gene expression during Arabidopsis seed filling," *Plant Cell*, 14:1191-1206, 2002.

Rylott et al., "Co-ordinate regulation of genes involved in storage lipid mobilization in *Arabidopsis thaliana*," *Biochem Soc. Trans.*, 29:283-287, 2001.

Schnarrenberger and Martin, "Evolution of the enzymes of the citric acid cycle and the glyoxylate cycle of high plants, A case study of endosymbiotic gene transfer," *Eur. J. Biochem.*, 269:868-883, 2002.

Schnurr et al., "Characterization of an acyl-CoA synthetase from *Arabidopsis thaliana.*," *Biochem Soc. Trans.*, 28(6):957-958, 2000.

Shockey et al., "Characterization of the AMP-binding protein gene family in *Arabidopsis thaliana*: will the real acyl-CoA synthetases please stand up?" *Biochem Soc. Trans.*, 28(6):955-957, 2000.

Thelen et al., "Biotin carboxyl carrier protein isoforms in Brassicaceae oilseeds," *Biochem. Soc. Trans.*, 28(6):595-598, 2000.

Theologis et al., "Sequence and analysis of chromosome 1 of the plant *Arabidopsis thaliana*," *Nature*, 408:816-820, 2000.

Wada et al., "Role of a positive regulator of root hair development, CAPRICE, in Arabidopsis root epidermal cell differentiation," *Development*, 129(23):5409-5419, 2002.

White et al., "A new set of Arabidopsis expressed sequence tags from developing seeds. The metabolic pathway from carbohydrates to seed oil," *Plant Physiol.*, 124:1582-1594, 2000.

Yadav et al., "Cloning of higher plant omega-3 fatty acid desaturases," *Plant Physiol.*, 103(2):467-476, 1993.

UNIPROT Accession No. Q3E6X4, Jan. 24, 2006, 1 page.

EMBL Accession No. CNS0ADSW, Feb. 6, 2004, 2 pages.

* cited by examiner

US 7,554,009 B2

GENERATION OF PLANTS WITH ALTERED OIL CONTENT

REFERENCE TO RELATED APPLICATIONS

This is the §371 U.S. National Stage of International Application No. PCT/US2005/018919, filed May 26, 2005, which was published in English under PCT Article 21(2), which in turn claims the benefit of U.S. Provisional Application No. 60/575,202, filed May 28, 2004, the contents of both of which are hereby incorporated by reference.

BACKGROUND OF THE INVENTION

The ability to manipulate the composition of crop seeds, particularly the content and composition of seed oils, has important applications in the agricultural industries, relating both to processed food oils and to oils for animal feeding. Seeds of agricultural crops contain a variety of valuable constituents, including oil, protein and starch. Industrial processing can separate some or all of these constituents for individual sale in specific applications. For instance, nearly 60% of the U.S. soybean crop is crushed by the soy processing industry. Soy processing yields purified oil, which is sold at high value, while the remainder is sold principally for lower value livestock feed (US Soybean Board, 2001 Soy Stats). Canola seed is crushed to produce oil and the co-product canola meal (Canola Council of Canada). Nearly 20% of the 1999/2000 US corn crop was industrially refined, primarily for production of starch, ethanol and oil (Corn Refiners Association). Thus, it is often desirable to maximize oil content of seeds. For instance, for processed oilseeds such as soy and canola, increasing the absolute oil content of the seed will increase the value of such grains. For processed corn it may be desired to either increase or decrease oil content, depending on utilization of other major constituents. Decreasing oil may improve the quality of isolated starch by reducing undesired flavors associated with oil oxidation. Alternatively, in ethanol production, where flavor is unimportant, increasing oil content may increase overall value. In many fed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors.

Biotechnological manipulation of oils can provide compositional alteration and improvement of oil yield. Compositional alterations include high oleic soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from about 3.5% to about 7%, improving the energy content of the grain.

While it has been fruitful, the HOC production system has inherent limitations. First, the system of having a low percentage of pollinators responsible for an entire field's seed set contains inherent risks, particularly in drought years. Second, oil contents in current HOC fields have plateaued at about 9% oil. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

The most obvious target crops for the processed oil market are soy and rapeseed, and a large body of commercial work (e.g., U.S. Pat. No. 5,952,544; PCT application WO9411516) demonstrates that *Arabidopsis* is an excellent model for oil metabolism in these crops. Biochemical screens of seed oil composition have identified *Arabidopsis* genes for many critical biosynthetic enzymes and have led to identification of agronomically important gene orthologs. For instance, screens using chemically mutagenized populations have identified lipid mutants whose seeds display altered fatty acid composition (Lemieux et al., 1990; James and Dooner, 1990). T-DNA mutagenesis screens (Feldmann et al., 1989) that detected altered fatty acid composition identified the omega 3 desaturase (FAD3) and delta-12 desaturase (FAD2) genes (U.S. Pat. No. 5,952,544; Yadav et al., 1993; Okuley et al., 1994). A screen which focused on oil content rather than oil quality, analyzed chemically-induced mutants for wrinkled seeds or altered seed density, from which altered seed oil content was inferred (Focks and Benning, 1998). Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al, 1995). It was further shown that seed-specific over-expression of the DGAT cDNA was associated with increased seed oil content (Jako et al., 2001).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., 1992; Weigel D et al. 2000). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., 1996, Schaffer et al., 1998, Fridborg et al., 1999; Kardailsky et al., 1999; Christensen S et al., 1998).

SUMMARY OF THE INVENTION

The invention provides a transgenic plant having a high oil phenotype. The transgenic plant comprises a transformation vector comprising a nucleotide sequence that encodes or is complementary to a sequence that encodes a HIO1002 polypeptide. In preferred embodiments, the transgenic plant is selected from the group consisting of rapeseed, soy, corn, sunflower, cotton, cocoa, safflower, oil palm, coconut palm, flax, castor and peanut. The invention further provides a method of producing oil comprising growing the transgenic plant and recovering oil from said plant.

The invention also provides a transgenic plant cell having a high oil phenotype. The transgenic plant cell comprises a transformation vector comprising a nucleotide sequence that encodes or is complementary to a sequence that encodes a High Oil (hereinafter "HIO1002") polypeptide. In preferred embodiments, the transgenic plant cell is selected from the group consisting of rapeseed, soy, corn, sunflower, cotton, cocoa, safflower, oil palm, coconut palm, flax, castor and peanut. In other embodiments, the plant cell is a seed, pollen, propagule, or embryo cell. The invention further provides feed, meal, grain, food, or seed comprising a nucleic acid sequence that encodes a HIO1002 polypeptide. The invention also provides feed, meal, grain, food, or seed comprising the HIO1002 polypeptide, or an ortholog thereof.

The transgenic plant of the invention is produced by a method that comprises introducing into progenitor cells of the plant a plant transformation vector comprising a nucleotide sequence that encodes or is complementary to a sequence that encodes a HIO1002 polypeptide, and growing the transformed progenitor cells to produce a transgenic plant, wherein the HIO1002 polynucleotide sequence is expressed causing the high oil phenotype. The invention further provides plant cells obtained from said transgenic plant.

The present invention also provides a container of over about 10,000, more preferably about 20,000, and even more preferably about 40,000 seeds where over about 10%, more preferably about 25%, more preferably about 50%, and even more preferably about 75% or more preferably about 90% of the seeds are seeds derived from a plant of the present invention.

The present invention also provides a container of over about 10 kg, more preferably about 25 kg, and even more preferably about 50 kg seeds where over about 10%, more preferably about 25%, more preferably about 50%, and even more preferably about 75% or more preferably about 90% of the seeds are seeds derived from a plant of the present invention.

Any of the plants or parts thereof of the present invention may be processed to produce a feed, meal, or oil preparation. A particularly preferred plant part for this purpose is a seed. In a preferred embodiment the feed, meal, or oil preparation is designed for ruminant animals. Methods to produce feed, meal, and oil preparations are known in the art. See, for example, U.S. Pat. Nos. 4,957,748; 5,100,679; 5,219,596; 5,936,069; 6,005,076; 6,146,669; and 6,156,227. The meal of the present invention may be blended with other meals. In a preferred embodiment, the meal produced from plants of the present invention or generated by a method of the present invention constitutes greater than about 0.5%, about 1%, about 5%, about 10%, about 25%, about 50%, about 75%, or about 90% by volume or weight of the meal component of any product. In another embodiment, the meal preparation may be blended and can constitute greater than about 10%, about 25%, about 35%, about 50%, or about 75% of the blend by volume.

DETAILED DESCRIPTION OF THE INVENTION

Definitions

Unless otherwise indicated, all technical and scientific terms used herein have the same meaning as they would to one skilled in the art of the present invention. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native plant.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequence.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus) as well as plant seeds, pollen, propagules and embryos.

As used herein, the terms "native" and "wild-type" relative to a given plant trait or phenotype refers to the form in which that trait or phenotype is found in the same variety of plant in nature.

As used herein, the term "modified" regarding a plant trait, refers to a change in the phenotype of a transgenic plant relative to the similar non-transgenic plant. An "interesting phenotype (trait)" with reference to a transgenic plant refers to an observable or measurable phenotype demonstrated by a T1 and/or subsequent generation plant, which is not displayed by the corresponding non-transgenic (i.e., a genotypically similar plant that has been raised or assayed under similar conditions). An interesting phenotype may represent an improvement in the plant or may provide a means to produce improvements in other plants. An "improvement" is a feature that may enhance the utility of a plant species or variety by providing the plant with a unique and/or novel quality. An "altered oil content phenotype" refers to measurable phenotype of a genetically modified plant, where the plant displays a statistically significant increase or decrease in overall oil content (i.e., the percentage of seed mass that is oil), as compared to the similar, but non-modified plant. A high oil phenotype refers to an increase in overall oil content.

As used herein, a "mutant" polynucleotide sequence or gene differs from the corresponding wild type polynucleotide sequence or gene either in terms of sequence or expression, where the difference contributes to a modified plant phenotype or trait. Relative to a plant or plant line, the term "mutant" refers to a plant or plant line which has a modified plant phenotype or trait, where the modified phenotype or trait is associated with the modified expression of a wild type polynucleotide sequence or gene.

As used herein, the term "T1" refers to the generation of plants from the seed of T0 plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. The class of plants which can be used in the methods of the present invention is generally as broad as the class of higher plants amenable to transformation techniques, including both monocotyledenous and dicotyledenous plants.

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed", "transfected", or "transgenic". Direct and indirect progeny of transformed plants or plant cells that also contain the heterologous polynucleotide are also considered transgenic.

Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) *Agrobacterium*-mediated transformation methods.

The most commonly used methods for transformation of plant cells are the *Agrobacterium*-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile-mediated delivery of the desired polynucleotide.

*Agrobacterium*-mediated transformation is achieved through the use of a genetically engineered soil bacterium belonging to the genus *Agrobacterium*. A number of wild-type and disarmed strains of *Agrobacterium tumefaciens* and *Agrobacterium rhizogenes* harboring Ti or Ri plasmids can be used for gene transfer into plants. Gene transfer is done via the transfer of a specific DNA known as "T-DNA" that can be genetically engineered to carry any desired piece of DNA into many plant species.

*Agrobacterium*-mediated genetic transformation of plants involves several steps. The first step, in which the virulent *Agrobacterium* and plant cells are first brought into contact with each other, is generally called "inoculation". Following the inoculation, the *Agrobacterium* and plant cells/tissues are permitted to be grown together for a period of several hours to several days or more under conditions suitable for growth and T-DNA transfer. This step is termed "co-culture". Following co-culture and T-DNA delivery, the plant cells are treated with bactericidal or bacteriostatic agents to kill the *Agrobacterium* remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microprojectile bombardment (U.S. Pat. No. 5,550,318 (Adams et al.); U.S. Pat. No. 5,538,880 (Lundquist et. al.), U.S. Pat. No. 5,610,042 (Chang et al.); and PCT Publication WO 95/06128 (Adams et al.); each of which is specifically incorporated herein by reference in its entirety), particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (International Publication No. WO 95/06128 (Adams et al.)), barley, wheat (U.S. Pat. No. 5,563,055 (Townsend et al) incorporated herein by reference in its entirety), rice, oat, rye, sugarcane, and sorghum; as well as a number of dicots including tobacco, soybean (U.S. Pat. No. 5,322,783 (Tomes et al.), incorporated herein by reference in its entirety), sunflower, peanut, cotton, tomato, and legumes in general (U.S. Pat. No. 5,563,055 (Townsend et al.) incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin (and neomycin, G418, bleomycin); methotrexate (and trimethoprim); chloramphenicol; kanamycin and tetracycline. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. No. 5,627,061 (Barry, et al.), U.S. Pat. No. 5,633,435 (Barry, et al.), and U.S. Pat. No. 6,040,497 (Spencer, et al.) and aroA described in U.S. Pat. No. 5,094,945 (Comai) for glyphosate tolerance; a polynucleotide molecule encoding bromoxynil nitrilase (Bxn) described in U.S. Pat. No. 4,810,648 (Duerrschnabel, et al.) for Bromoxynil tolerance; a polynucleotide molecule encoding phytoene desaturase (crtI) described in Misawa et al, (1993) Plant J. 4:833-840 and Misawa et al, (1994) Plant J. 6:481-489 for norflurazon tolerance; a polynucleotide molecule encoding acetohydroxyacid synthase (AHAS, aka ALS) described in Sathasiivan et al. (1990) Nucl. Acids Res. 18:2188-2193 for tolerance to sulfonylurea herbicides; and the bar gene described in DeBlock, et al. (1987) EMBO J. 6:2513-2519 for glufosinate and bialaphos tolerance.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, Physiol. Plant, 15:473-497, 1962) or N6-based media (Chu et al., Scientia Sinica 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

One of ordinary skill will appreciate that, after an expression cassette is stably incorporated in transgenic plants and confirmed to be operable, it can be introduced into other plants by sexual crossing. Any of a number of standard breeding techniques can be used, depending upon the species to be crossed.

Identification of Plants with an Altered Oil Content Phenotype

We used an *Arabidopsis* activation tagging screen to identify the association between the gene we have identified and designated "HIO1002," (At1g73650, GI#30698954) encoding a protein (GI#18410409), and an altered oil content phenotype (specifically, a high oil phenotype). Splice variants and their corresponding GenBank entries are noted below. Briefly, and as further described in the Examples, a large number of *Arabidopsis* plants were mutated with the pSKI015 vector, which comprises a T-DNA from the Ti plasmid of *Agrobacterium tumifaciens*, a viral enhancer element, and a selectable marker gene (Weigel et al., 2000). When the T-DNA inserts into the genome of transformed plants, the enhancer element can cause up-regulation genes in the vicinity, generally within about 10 kilobase (kb) of the insertion. T1 plants were exposed to the selective agent in order to specifically recover transformed plants that expressed the selectable marker and therefore harbored T-DNA insertions. Samples of approximately 15-20 T2 seeds were collected from transformed T1 plants, and lipids were extracted from whole seeds. Gas chromatography (GC) analysis was performed to determine fatty acid content and composition of seed samples.

An *Arabidopsis* line that showed a high-oil phenotype was identified. The association of the HIO1002 gene with the high oil phenotype was discovered by analysis of the genomic DNA sequence flanking the T-DNA insertion in the identified line. Accordingly, HIO1002 genes and/or polypeptides may be employed in the development of genetically modified plants having a modified oil content phenotype ("a HIO1002 phenotype"). HIO1002 genes may be used in the generation of oilseed crops that provide improved oil yield from oilseed processing and in the generation of feed grain crops that provide increased energy for animal feeding. HIO1002 genes may further be used to increase the oil content of specialty oil crops, in order to augment yield of desired unusual fatty acids. Transgenic plants that have been genetically modified to express HIO1002 can be used in the production of oil, wherein the transgenic plants are grown, and oil is obtained from plant parts (e.g. seed) using standard methods.

HIO1002 Nucleic Acids and Polypeptides

*Arabidopsis* HIO1002 nucleic acid sequence is provided in SEQ ID NO: 1 and in Genbank entry GI#30698954. The corresponding protein sequence is provided in SEQ ID NO:2 and in GI#18410409. Two putative splice variants were also identified which encode proteins that differ from SEQ ID NO:2 at the COOH terminus: GI#30698952 (SEQ ID NO:3) with a corresponding protein sequence as in GI#30698953 (SEQ ID NO:4) that is 100% identical with SEQ ID NO:2 up to E288, and ending with LG at amino acid positions 289 and 290, respectively; and GI#42572098 (SEQ ID NO:5) with a corresponding protein sequence as in GI#42572099 (SEQ ID NO:6) that is 100% identical with SEQ ID NO:2 up to E288, and ending with GRLQNSKEKEVKDD at amino acids 289-302, respectively. Nucleic acids and/or proteins that are orthologs or paralogs of *Arabidopsis* HIO11002, are described in Example 3 below.

As used herein, the term "HIO1002 polypeptide" refers to a full-length HIO1002 protein or a fragment, derivative (variant), or ortholog thereof that is "functionally active," meaning that the protein fragment, derivative, or ortholog exhibits one or more or the functional activities associated with the polypeptide of SEQ ID NO:2, 4, or 6. In one preferred embodiment, a functionally active HIO1002 polypeptide causes an altered oil content phenotype when mis-expressed in a plant. In a further preferred embodiment, mis-expression of the HIO1002 polypeptide causes a high oil phenotype in a plant. In another embodiment, a functionally active HIO1002 polypeptide is capable of rescuing defective (including deficient) endogenous HIO1002 activity when expressed in a plant or in plant cells; the rescuing polypeptide may be from the same or from a different species as that with defective activity. In another embodiment, a functionally active fragment of a full length HIO1002 polypeptide (i.e., a native polypeptide having the sequence of SEQ ID NO:2, 4, or 6, or a naturally occurring ortholog thereof) retains one or more of the biological properties associated with the full-length HIO1002 polypeptide, such as signaling activity, binding activity, catalytic activity, or cellular or extra-cellular localizing activity. A HIO1002 fragment preferably comprises a HIO1002 domain, such as a C- or N-terminal or catalytic domain, among others, and preferably comprises at least 10, preferably at least 20, more preferably at least 25, and most preferably at least 50 contiguous amino acids of a HIO1002 protein. Functional domains can be identified using the PFAM program (Bateman A et al., 1999 Nucleic Acids Res 27:260-262). A preferred HIO1002 fragment comprises of one or more transmembrane domains.

Functionally active variants of full-length HIO1002 polypeptides or fragments thereof include polypeptides with amino acid insertions, deletions, or substitutions that retain one of more of the biological properties associated with the full-length HIO1002 polypeptide. In some cases, variants are generated that change the post-translational processing of a HIO1002 polypeptide. For instance, variants may have altered protein transport or protein localization characteristics or altered protein half-life compared to the native polypeptide.

As used herein, the term "HIO1002 nucleic acid" encompasses nucleic acids with the sequence provided in or complementary to the sequence provided in SEQ ID NO: 1, 3, or 5, as well as functionally active fragments, derivatives, or orthologs thereof. A HIO1002 nucleic acid of this invention may be DNA, derived from genomic DNA or cDNA, or RNA.

In one embodiment, a functionally active HIO1002 nucleic acid encodes or is complementary to a nucleic acid that encodes a functionally active HIO1002 polypeptide. Included within this definition is genomic DNA that serves as a template for a primary RNA transcript (i.e., an mRNA precursor) that requires processing, such as splicing, before encoding the functionally active HIO1002 polypeptide. A HIO1002 nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed HIO1002 polypeptide, or an intermediate form. A HIO1002 polynucleotide can also include heterologous coding sequences, for example, sequences that encode a marker included to facilitate the purification of the fused polypeptide, or a transformation marker.

In another embodiment, a functionally active HIO1002 nucleic acid is capable of being used in the generation of loss-of-function HIO1002 phenotypes, for instance, via antisense suppression, co-suppression, etc.

In one preferred embodiment, a HIO1002 nucleic acid used in the methods of this invention comprises a nucleic acid sequence that encodes or is complementary to a sequence that encodes a HIO1002 polypeptide having at least 50%, 60%, 70%, 75%, 80%, 85%, 90%, 95% or more sequence identity to the polypeptide sequence presented in SEQ ID NO:2, 4 or 6.

In another embodiment a HIO1002 polypeptide of the invention comprises a polypeptide sequence with at least 50% or 60% identity to the HIO1002 polypeptide sequence of SEQ ID NO:2, 4 or 6, and may have at least 70%, 80%, 85%, 90% or 95% or more sequence identity to the HIO1002 polypeptide sequence of SEQ ID NO:2, 4, or 6, such as one or more transmembrane domains. In another embodiment, a HIO1002 polypeptide comprises a polypeptide sequence with at least 50%, 60%, 70%, 80%, 85%, 90% or 95% or more sequence identity to a functionally active fragment of the polypeptide presented in SEQ ID NO:2, 4, or 6. In yet another embodiment, a HIO1002 polypeptide comprises a polypeptide sequence with at least 50%, 60%, 70%, 80%, or 90% identity to the polypeptide sequence of SEQ ID NO:2, 4 or 6 over its entire length and comprises of one or more transmembrane domains.

In another aspect, a HIO1002 polynucleotide sequence is at least 50% to 60% identical over its entire length to the HIO1002 nucleic acid sequence presented as SEQ ID NO: 1, 3, or 5, or nucleic acid sequences that are complementary to such a HIO1002 sequence, and may comprise at least 70%, 80%, 85%, 90% or 95% or more sequence identity to the HIO1002 sequence presented as SEQ ID NO: 1, 3, or 5, or a functionally active fragment thereof, or complementary sequences.

As used herein, "percent (%) sequence identity" with respect to a specified subject sequence, or a specified portion thereof, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that selectively hybridize to the nucleic acid sequence of SEQ ID NO: 1. The stringency of hybridization can be controlled by temperature, ionic strength, pH, and the presence of denaturing agents such as formamide during hybridization and washing. Conditions routinely used are well known (see, e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of SEQ ID NO: 1 under stringent hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5× Denhardt's solution, 0.05% sodium pyrophosphate and 100 µg/ml herring sperm DNA; hybridization for 18-20 hours at 65° C. in a solution containing 6×SSC, 1× Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5×SSC, 50 mM Tris-HCI (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCI (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5× Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding a HIO1002 polypeptide can be produced. For example, codons may be selected to increase the rate at which expression of the polypeptide occurs in a particular host species, in accordance with the optimum codon usage dictated by the particular host organism (see, e.g., Nakamura et al, 1999). Such sequence variants may be used in the methods of this invention.

The methods of the invention may use orthologs of the *Arabidopsis* HIO1002. Methods of identifying the orthologs in other plant species are known in the art. Normally, orthologs in different species retain the same function, due to presence of one or more protein motifs and/or 3-dimensional structures. In evolution, when a gene duplication event follows speciation, a single gene in one species, such as *Arabidopsis*, may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210).

Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, 1989; Dieffenbach and Dveksler, 1995). For instance, methods for generating a cDNA library from the plant species of interest and probing the library with partially homologous gene probes are described in Sambrook et al. A highly conserved portion of the *Arabidopsis* HIO1002 coding sequence may be used as a probe. HIO1002 ortholog nucleic acids may hybridize to the nucleic acid of SEQ ID NO:1 under high, moderate, or low stringency conditions. After amplification or isolation of a segment of a putative ortholog, that segment may be cloned and sequenced by standard techniques and utilized as a probe to isolate a complete cDNA or genomic clone. Alternatively, it is possible to initiate an EST project to generate a database of sequence information for the plant species of interest. In another approach, antibodies that specifically bind known HIO1002 polypeptides are used for ortholog isolation (see, e.g., Harlow and Lane, 1988, 1999). Western blot analysis can determine that a HIO1002 ortholog (i.e., an orthologous protein) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., 1989. Once the candidate ortholog(s) are identified by any of these means, candidate orthologous sequence are used as bait (the "query") for the reverse BLAST against sequences from *Arabidopsis* or other species in which HIO1002 nucleic acid and/or polypeptide sequences have been identified.

HIO1002 nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., 1991), may be used to introduce desired changes into a cloned nucleic acid.

In general, the methods of the invention involve incorporating the desired form of the HIO1002 nucleic acid into a plant expression vector for transformation of in plant cells, and the HIO1002 polypeptide is expressed in the host plant.

An isolated HIO1002 nucleic acid molecule is other than in the form or setting in which it is found in nature and is identified and separated from least one contaminant nucleic acid molecule with which it is ordinarily associated in the natural source of the HIO1002 nucleic acid. However, an isolated HIO1002 nucleic acid molecule includes HIO1002 nucleic acid molecules contained in cells that ordinarily express HIO1002 where, for example, the nucleic acid molecule is in a chromosomal location different from that of natural cells.

Generation of Genetically Modified Plants with an Altered Oil Content Phenotype

HIO1002 nucleic acids and polypeptides may be used in the generation of genetically modified plants having a modified oil content phenotype. As used herein, a "modified oil content phenotype" may refer to modified oil content in any part of the plant; the modified oil content is often observed in seeds. In a preferred embodiment, altered expression of the HIO1002 gene in a plant is used to generate plants with a high oil phenotype.

The methods described herein are generally applicable to all plants. Although activation tagging and gene identification is carried out in *Arabidopsis*, the HIO1002 gene (or an ortholog, variant or fragment thereof) may be expressed in any type of plant. In a preferred embodiment, the invention is directed to oil-producing plants, which produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The invention may also be directed to fruit- and vegetable-bearing plants, grain-producing plants, nut-producing plants, rapid cycling *Brassica* species, alfalfa (*Medicago sativa*), tobacco (*Nicotiana*), turfgrass (Poaceae family), other forage crops, and wild species that may be a source of unique fatty acids.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to *Agrobacterium*-mediated transformation, electroporation, microinjection, microprojectile bombardment calcium-phosphate-DNA co-precipitation or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising an HIO1002 polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.). A construct or vector may include a plant promoter to express the nucleic acid molecule of choice. In a preferred embodiment, the promoter is a plant promoter.

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as rapeseed (De Block et al., 1989), sunflower (Everett et al., 1987), and soybean (Christou et al., 1989; Kline et al., 1987).

Expression (including transcription and translation) of HIO1002 may be regulated with respect to the level of expression, the tissue type(s) where expression takes place and/or developmental stage of expression. A number of heterologous regulatory sequences (e.g., promoters and enhancers) are available for controlling the expression of a HIO1002 nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the nopaline synthase (NOS) promoter (Ebert et al., *Proc. Natl. Acad. Sci. (U.S.A.)* 84:5745-5749, 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324, 1987) and the CaMV 35S promoter (Odell et al., *Nature* 313:810-812, 1985 and Jones JD et al, 1992), the melon actin promoter (published PCT application WO0056863), the figwort mosaic virus 35S-promoter (U.S. Pat. No. 5,378,619), the light-inducible promoter from the small subunit of ribulose-1,5-bis-phosphate carboxylase (ssRUBISCO), the Adh promoter (Walker et al., *Proc. Natl. Acad. Sci. (U.S.A.)* 84:6624-6628, 1987), the sucrose synthase promoter (Yang et al., *Proc. Natl Acad. Sci. (U.S.A.)* 87:4144-4148, 1990), the R gene complex promoter (Chandler et al., *The Plant Cell* 1:1175-1183, 1989), the chlorophyll a/b binding protein gene promoter the CsVMV promoter (Verdaguer B et al., 1998); these promoters have been used to create DNA constructs that have been expressed in plants, e.g., PCT publication WO 84/02913. Exemplary tissue-specific promoters include the tomato E4 and E8 promoters (U.S. Pat. No. 5,859,330) and the tomato 2AII gene promoter (Van Haaren M J J et al., 1993).

In one preferred embodiment, HIO1002 expression is under control of regulatory sequences from genes whose expression is associated with early seed and/or embryo development. Indeed, in a preferred embodiment, the promoter used is a seed-enhanced promoter. Examples of such promoters include the 5' regulatory regions from such genes as napin (Kridl et al., *Seed Sci. Res.* 1:209:219, 1991), globulin (Belanger and Kriz, *Genet.*, 129: 863-872, 1991, GenBank Accession No. L22295), gamma zein Z 27 (Lopes et al., *Mol Gen Genet.*, 247:603-613, 1995), L3 oleosin promoter (U.S. Pat. No. 6,433,252), phaseolin (Bustos et al., *Plant Cell*, 1(9):839-853, 1989), arcelin5 (US 2003/0046727), a soybean 7S promoter, a 7Sα promoter (US 2003/0093828), the soybean 7Sα' beta conglycinin promoter, a 7S α' promoter (Beachy et al., *EMBO J,* 4:3047, 1985; Schuler et al., *Nucleic Acid Res.*, 10(24):8225-8244, 1982), soybean trypsin inhibitor (Riggs et al., *Plant Cell* 1(6):609-621, 1989), ACP (Baerson et al., *Plant Mol. Biol.*, 22(2):255-267, 1993), stearoyl-ACP desaturase (Slocombe et al., *Plant Physiol.* 104(4):167-176, 1994), soybean a' subunit of β-conglycinin (Chen et al., *Proc. Natl. Acad. Sci.* 83:8560-8564, 1986), *Vicia faba* USP (β-Vf.Usp, SEQ ID NO: 1, 2, and 3 in (US 2003/229918) and *Zea mays* L3 oleosin promoter (Hong et al., *Plant Mol. Biol.*, 34(3):549-555, 1997). Also included are the zeins, which are a group of storage proteins found in corn endosperm. Genomic clones for zein genes have been isolated (Pedersen et al., *Cell* 29:1015-1026, 1982; and Russell et al., *Transgenic Res.* 6(2):157-168) and the promoters from these clones, including the 15 kD, 16 kD, 19 kD, 22 kD, 27 kD and genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. Legume genes whose promoters are associated with early seed and embryo development include *V. faba* legumin (Baumlein et al., 1991, Mol Gen Genet 225: 121-8; Baumlein et al., 1992, Plant J 2:233-9), *V. faba* usp (Fiedler et al., 1993, Plant Mol Biol 22:669-79), pea convicilin (Bown et al., 1988, Biochem J 251:717-26), pea lectin (dePater et al., 1993, Plant Cell 5:877-86), *P. vulgaris* beta phaseolin (Bustos et al., 1991, EMBO J 10: 1469-79), *P. vulgaris* DLEC2 and PHS [beta] (Bobb et al, 1997, Nucleic Acids Res 25:641-7), and soybean beta-Conglycinin, 7S storage protein (Chamberland et al., 1992, Plant Mol Biol 19:93749).

Cereal genes whose promoters are associated with early seed and embryo development include rice glutelin ("GluA-3,"Yoshihara and Takaiwa, 1996, Plant Cell Physiol 37:107-11; "GluB-1," Takaiwa et al., 1996, Plant Mol Biol 30:1207-21; Washida et al., 1999, Plant Mol Biol 40:1-12; "Gt3," Leisy et al., 1990, Plant Mol Biol 14:41-50), rice prolamin (Zhou & Fan, 1993, Transgenic Res 2:141-6), wheat prolamin (Hammond-Kosack et al., 1993, EMBO J 12:545-54), maize zein (Z4, Matzke et al., 1990, Plant Mol Biol 14:323-32), and barley B-hordeins (Entwistle et al., 1991, Plant Mol Biol 17:1217-31).

Other genes whose promoters are associated with early seed and embryo development include oil palm GLO7A (7S globulin, Morcillo et al., 2001, Physiol Plant 112:233-243), *Brassica napus* napin, 2S storage protein, and napA gene (Josefsson et al., 1987, J Biol Chem 262:12196-201; Stalberg et al., 1993, Plant Mol Biol 1993 23:671-83; Ellerstrom et al., 1996, Plant Mol Biol 32:1019-27), *Brassica napus* oleosin (Keddie et al., 1994, Plant Mol Biol 24:327-40), *Arabidopsis* oleosin (Plant et al., 1994, Plant Mol Biol 25:193-205), *Arabidopsis* FAE1 (Rossak et al., 2001, Plant Mol Biol 46:717-25), *Canavalia gladiata* conA (Yamamoto et al., 1995, Plant Mol Biol 27:729-41), and *Catharanthus roseus* strictosidine synthase (Str, Ouwerkerk and Memelink, 1999, Mol Gen Genet 261:635-43). In another preferred embodiment, regulatory sequences from genes expressed during oil biosynthesis are used (see, e.g., U.S. Pat. No. 5,952,544). Alternative promoters are from plant storage protein genes (Bevan et al, 1993, Philos Trans R Soc Lond B Biol Sci 342:209-15). Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436.

In yet another aspect, in some cases it may be desirable to inhibit the expression of endogenous HIO1002 in a host cell. Exemplary methods for practicing this aspect of the invention include, but are not limited to antisense suppression (Smith, et al., 1988; van der Krol et al., 1988); co-suppression (Napoli, et al., 1990); ribozymes (PCT Publication WO 97/10328); and combinations of sense and antisense (Waterhouse, et al., 1998). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., 1988), a partial cDNA sequence including fragments of 5' coding sequence, (Cannon et al., 1990), or 3' non-coding sequences (Ch'ng et al., 1989). Cosuppression techniques may use the entire cDNA sequence (Napoli et al., 1990; van der Krol et al., 1990), or a partial cDNA sequence (Smith et al., 1990).

Standard molecular and genetic tests may be performed to further analyze the association between a gene and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include overexpression, ectopic expression, expression in other plant species and gene knock-out (reverse genetics, targeted knock-out, viral induced gene silencing [VIGS, see Baulcombe D, 1999]).

In a preferred application expression profiling, generally by microarray analysis, is used to simultaneously measure differences or induced changes in the expression of many different genes. Techniques for microarray analysis are well known in the art (Schena M et al., Science (1995) 270:467-470; Baldwin D et al., 1999; Dangond F, Physiol Genomics (2000) 2:53-58; van Hal N L et al., J Biotechnol (2000) 78:271-280; Richmond T and Somerville S, Curr Opin Plant Biol (2000) 3:108-116). Expression profiling of individual tagged lines may be performed. Such analysis can identify other genes that are coordinately regulated as a consequence of the overexpression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with an Altered Oil Content Phenotype

The invention further provides a method of identifying plants that have mutations in endogenous HIO1002 that confer altered oil content, and generating altered oil content progeny of these plants that are not genetically modified. In one method, called "TILLING" (for targeting induced local lesions in genomes), mutations are induced in the seed of a plant of interest, for example, using EMS treatment. The resulting plants are grown and self-fertilized, and the progeny are used to prepare DNA samples. HIO1002-specific PCR is used to identify whether a mutated plant has a HIO1002 mutation. Plants having HIO1002 mutations may then be tested for altered oil content, or alternatively, plants may be tested for altered oil content, and then HIO1002-specific PCR is used to determine whether a plant having altered oil content has a mutated HIO1002 gene. TILLING can identify mutations that may alter the expression of specific genes or the activity of proteins encoded by these genes (see Colbert et al (2001) Plant Physiol 126:480-484; McCallum et al (2000) Nature Biotechnology 18:455-457).

In another method, a candidate gene/Quantitative Trait Locus (QTLs) approach can be used in a marker-assisted breeding program to identify alleles of or mutations in the HIO1002 gene or orthologs of HIO1002 that may confer altered oil content (see Bert et al., Theor Appl Genet. 2003 June; 107(1):181-9; and Lionneton et al, Genome. 2002 December; 45(6):1203-15). Thus, in a further aspect of the invention, a HIO1002 nucleic acid is used to identify whether a plant having altered oil content has a mutation in endogenous HIO1002 or has a particular allele that causes altered oil content.

While the invention has been described with reference to specific methods and embodiments, it will be appreciated that various modifications and changes may be made without departing from the invention. All publications cited herein are expressly incorporated herein by reference for the purpose of describing and disclosing compositions and methodologies that might be used in connection with the invention. All cited patents, patent applications, and sequence information in referenced websites and public databases are also incorporated by reference.

EXAMPLES

Example 1

Generation of Plants with a HIO1002 Phenotype by Transformation with an Activation Tagging Construct Mutants were generated using the activation tagging "ACT-TAG" vector, pSKI015 (GI#6537289; Weigel D et al., 2000). Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4×CaMV 35S enhancer element. Transgenic plants were selected at the T1 generation based on herbicide resistance.

T3 seed was analyzed by Near Infrared Spectroscopy (NIR) at the time of harvest. NIR infrared spectra were captured using a Bruker 22 N/F. Bruker Software was used to estimate total seed oil and total seed protein content using data from NIR analysis and reference methods according to the manufacturers instructions. Oil contents predicted by our calibration (ren oil 1473 1d+sline.q2, Predicts Hexane Extracted Oil), which followed the general method of AOCS Procedure AM1-92, Official Methods and Recommended Practices of the American Oil Chemists Society, 5th Ed., AOCS, Champaign, Ill., were compared for 38,090 individual ACTTAG lines. Subsequent to seed compositional analysis, the position of the ACTTAG element in the genome of in each line was determined by inverse PCR and sequencing. 38,090 lines with recovered flanking sequences were considered in this analysis.

Since the 38,090 lines were planted and grown over a 12-month period, the seed oil content values were normalized to minimize the effect of environmental differences which may alter seed oil content. The average seed oil content and its standard deviation, for each day lines were planted, were calculated. The seed oil content was expressed as a "relative standard deviation distance" (SD distance) which was calculated by subtracting the average seed oil content for the planting day from seed oil content for each line and dividing the difference by the standard deviation for that day. This normalization allows comparison of seed oil content in seed from plants grown throughout the year.

Genes that cause a high seed oil phenotype when over-expressed were identified by evaluating all of the genes affected by ACTTAG elements in the 38,090 lines. This was accomplished by the following procedure; first, the genes likely to be activated by the ACTTAG element in each line were identified and the seed oil content of the line was assigned to these genes; second, the seed oil content when a particular gene is over-expressed was determined by averaging the individual seed oil values for each gene. Since 38,090 lines were evaluated and each element affects an average of 2.5 genes, each gene will have an average of 4 seed oil values. The genes with the highest average SD distance were determined to be those that cause a high seed oil phenotype when over-expressed.

Seed from plants over-expressing At1g73650 have an oil content of 128% of the planting day average, as is shown in the following Table 1.

TABLE 1

| Tair | relative standard deviation distance | plant count | Description | Line ID | Planting date | n (# of ACTTAG lines planted for the date with NIR measurement) | Seed Oil content (%) | Average oil content of the planting date (%) | Standard deviation of the oil content for the planting date |
|---|---|---|---|---|---|---|---|---|---|
| At1g73650 | 2.960951 | 1 | expressed protein | W000203274 | Oct. 7, 2002 | 1184 | 32.016 | 25.025 | 2.361 |

Example 2

Characterization of the T-DNA Insertion in Plants Exhibiting the Altered Oil Content Phenotype.

We performed standard molecular analyses, essentially as described in patent application PCT WO0183697, to determine the site of the T-DNA insertion associated with the altered oil content phenotype. Briefly, genomic DNA was extracted from plants exhibiting the altered oil content phenotype. PCR, using primers specific to the pSKI015 vector, confirmed the presence of the 35S enhancer in plants from the HIO1002 oil line, and Southern blot analysis verified the genomic integration of the ACTTAG T-DNA and showed the presence of the T-DNA insertions in each of the transgenic lines.

Inverse PCR was used to recover genomic DNA flanking the T-DNA insertion, which was then subjected to sequence analysis using a basic BLASTN search and/or a search of the *Arabidopsis* Information Resource (TAIR) database (available at the arabidopsis.org website).

Example 3

Recapitulation of HIO1002 Phenotype

To test whether over-expression of At1g73650 causes a high seed oil phenotype, oil content in seeds from transgenic plants over-expressing this gene was compared with oil content in seeds from non-transgenic control plants. To do this, At1g73650 was cloned into a plant transformation vector behind the seed specific CsVMV promoter and transformed into *Arabidopsis* plants using the floral dip method. The plant transformation vector contains the nptII gene driven by the RE4 promoter, to provide resistance to kanamycin, and serve as a selectable marker. Seed from the transformed plants were plated on agar medium containing kanamycin. After 7 days, transgenic plants were identified as healthy green plants and transplanted to soil. Non-transgenic control plants were germinated on agar medium, allowed to grow for 7 days and then transplanted to soil. Twenty-two transgenic seedlings and 10 non-transgenic control plants were transplanted to random positions in the same 32 cell flat. The plants were grown to maturity, allowed to self-fertilize and set seed. Seed was harvested from each plant and its oil content estimated by Near Infrared (NIR) Spectroscopy using methods previously described. The percent oil in the seed harvested from each plant as determined by NIR spectroscopy is presented in Table 3. The Relative Oil value is determined by dividing the predicted oil value by the average oil value in control seed (i.e. seed from plants without the trangene).

The effect of over-expression of At1g73650 on seed oil has been tested in two experiments. In both experiments, the plants over-expressing At1g73650 had higher seed oil content than the control plants grown in the same flat. Across the experiments, the average seed oil content of plants over-expressing At1g73650 was 4.5% greater than the untransformed controls. The seed oil content in plants over-expressing At1g73650 was significantly greater than non-transgenic control plants (two-way ANOVA; P=0.0160).

TABLE 2

| Experiment | Plant | Transgene | Percent Oil | Relative Oil |
|---|---|---|---|---|
| 1 | DX07122001 | CsVMV:At1g73650 | 29.89 | 110.48 |
| 1 | DX07122002 | CsVMV:At1g73650 | 26.7 | 98.68 |
| 1 | DX07122003 | CsVMV:At1g73650 | 27.33 | 101.03 |
| 1 | DX07122004 | CsVMV:At1g73650 | 26.13 | 96.59 |
| 1 | DX07122005 | CsVMV:At1g73650 | 24.09 | 89.04 |
| 1 | DX07122006 | CsVMV:At1g73650 | 27.38 | 101.2 |
| 1 | DX07122007 | CsVMV:At1g73650 | 30.58 | 113.05 |
| 1 | DX07122009 | CsVMV:At1g73650 | 28.05 | 103.68 |
| 1 | DX07122010 | CsVMV:At1g73650 | 28.15 | 104.06 |
| 1 | DX07122011 | CsVMV:At1g73650 | 26 | 96.11 |
| 1 | DX07122012 | CsVMV:At1g73650 | 25.16 | 93 |
| 1 | DX07122013 | CsVMV:At1g73650 | 25.64 | 94.78 |
| 1 | DX07122014 | CsVMV:At1g73650 | 27.04 | 99.97 |
| 1 | DX07122015 | CsVMV:At1g73650 | 25.86 | 95.6 |
| 1 | DX07122016 | CsVMV:At1g73650 | 26.26 | 97.08 |
| 1 | DX07122017 | CsVMV:At1g73650 | 30.09 | 111.23 |
| 1 | DX07122018 | CsVMV:At1g73650 | 28.19 | 104.22 |
| 1 | DX07122019 | CsVMV:At1g73650 | 29.95 | 110.7 |
| 1 | DX07122020 | CsVMV:At1g73650 | 29 | 107.18 |
| 1 | DX07122021 | CsVMV:At1g73650 | 28.88 | 106.77 |
| 1 | DX07122022 | CsVMV:At1g73650 | 27.29 | 100.88 |
| 1 | DX07140001 | None | 26.33 | 97.33 |
| 1 | DX07140002 | None | 26.54 | 98.12 |
| 1 | DX07140003 | None | 28.19 | 104.21 |
| 1 | DX07140004 | None | 26.17 | 96.72 |
| 1 | DX07140005 | None | 26.05 | 96.29 |
| 1 | DX07140006 | None | 25.39 | 93.86 |
| 1 | DX07140007 | None | 25.87 | 95.64 |
| 1 | DX07140008 | None | 31.93 | 118.04 |
| 1 | DX07140009 | None | 28.13 | 103.99 |
| 1 | DX07140010 | None | 25.92 | 95.79 |
| 2 | DX07167001 | CsVMV:At1g73650 | 31.77 | 106.66 |
| 2 | DX07167002 | CsVMV:At1g73650 | 32.21 | 108.14 |
| 2 | DX07167003 | CsVMV:At1g73650 | 31.63 | 106.18 |
| 2 | DX07167004 | CsVMV:At1g73650 | 30.2 | 101.37 |
| 2 | DX07167005 | CsVMV:At1g73650 | 30.5 | 102.4 |
| 2 | DX07167006 | CsVMV:At1g73650 | 31.62 | 106.17 |
| 2 | DX07167007 | CsVMV:At1g73650 | 30.55 | 102.57 |
| 2 | DX07167008 | CsVMV:At1g73650 | 36.57 | 122.77 |
| 2 | DX07167009 | CsVMV:At1g73650 | 32.7 | 109.78 |
| 2 | DX07167010 | CsVMV:At1g73650 | 29.27 | 98.25 |
| 2 | DX07167011 | CsVMV:At1g73650 | 30 | 100.71 |
| 2 | DX07167012 | CsVMV:At1g73650 | 29.58 | 99.29 |
| 2 | DX07167013 | CsVMV:At1g73650 | 33.75 | 113.31 |
| 2 | DX07167014 | CsVMV:At1g73650 | 30.63 | 102.84 |
| 2 | DX07167015 | CsVMV:At1g73650 | 35.07 | 117.74 |
| 2 | DX07167016 | CsVMV:At1g73650 | 34.49 | 115.79 |
| 2 | DX07167017 | CsVMV:At1g73650 | 32.99 | 110.75 |
| 2 | DX07167018 | CsVMV:At1g73650 | 33.06 | 110.99 |
| 2 | DX07167019 | CsVMV:At1g73650 | 31.52 | 105.8 |
| 2 | DX07167020 | CsVMV:At1g73650 | 32.8 | 110.13 |
| 2 | DX07167022 | CsVMV:At1g73650 | 30.37 | 101.94 |
| 2 | DX07185001 | None | 29.9 | 100.39 |
| 2 | DX07185002 | None | 28.47 | 95.59 |
| 2 | DX07185003 | None | 28.83 | 96.79 |
| 2 | DX07185004 | None | 29.03 | 97.45 |
| 2 | DX07185005 | None | 29.05 | 97.51 |
| 2 | DX07185007 | None | 27.27 | 91.56 |
| 2 | DX07185008 | None | 31.06 | 104.26 |
| 2 | DX07185009 | None | 32.22 | 108.18 |
| 2 | DX07185010 | None | 32.25 | 108.28 |

Example 4

Analysis of *Arabidopsis* HIO1002 Sequence

Sequence analyses were performed with BLAST (Altschul et al., 1990, J. Mol. Biol. 215:403-410), PFAM (Bateman et al., 1999, Nucleic Acids Res 27:260-262), PSORT (Nakai K, and Horton P, 1999, Trends Biochem Sci 24:34-6), and/or CLUSTAL (Thompson J D et al., 1994, Nucleic Acids Res 22:4673-4680).

TBLASTN Against ESTs:

The candidate gene At1g73650 is supported by the full-length cDNAs GI:15809973 and GI:27363285. There are many ESTs from diverse plant species showing similarity to At1g73650. Where possible, ESTs contigs of each species were made. The top hit for each of the following species are listed below and included in the orthologue Table 2: *Triticum aestivum, Glycine max, Mentha×piperita, Populus tremula, Oryza sativa, Lycopersicon esculentum, Solanum tuberosum,* and *Beta vulgaris.*

1. Sugar Beet ESTs with the Following GenBank IDS:
gi|26121630
2. Potato ESTs with the Following GenBank IDS:
gi|12588047
gi|15259347
3. Tomato ESTs with the Following GenBank IDS:
gi|5896833
gi|5896833
gi|5896833
gi|12628275
gi|12628275
gi|12628275
gi|16242572
4. Rice ESTs with the Following GenBank IDS:
gi|5456487
gi|13420908
gi|700187
5. Poplar ESTs with the Following GenBank IDS:
gi|3857688
gi|23959842
gi|23960044
gi|23963690
gi|23997967
gi|23998879
gi|24062476
gi|24065210
gi|28609230
6. Soybean ESTs with the Following GenBank IDS:
gi|9205433
gi|12488109
gi|12773915
gi|15286042
gi|18731515
7. Corn ESTs with the Following GenBank IDS:
gi|5739680
gi|21208932
gi|407242
gi|407243
8. Cotton ESTs with the Following GenBank IDS:
gi|3326250
9. Wheat ESTs with the Following GenBank IDS:
gi|9742370
gi|20309688
gi|25194283
gi|25235692
gi|25237006
gi|25243036
gi|25261519
gi|25280706
gi|25431065
gi|25547029
gi|25560875
gi|32546080
gi|32670437

BLASTP Against Amino Acids:

The protein At1g73650 has homology to proteins from other organisms. The top seven BLAST results for At1g73650 are listed below and are included in the Orthologue Table 2 below.

1. One EST contig from *Beta vulgaris* ex|13978852|exs|13978851
2. One EST contig from *Solanum tubersom* ex|11208765|exs|11208764
3. One EST contig from *Lycopersicon esculentum* ex|5891894|exs|5891893
4. One EST contig from *Oryza sativa* ex|7258057|exs|7258056
5. One EST contig from *Populus tremula* ex|10187045|exs|10187044
6. One EST contig from *Glycine max* ex|9156811|exs|9156810
7. One EST contig from *Zea mays* ex|7766057|exs|7766056
8. One EST contig from *Gossypium hirsutum* ex|9283238|exs|9283237
9. One EST contig from *Triticum aestivum* ex|11024927|exs|1024926

TABLE 3

| Ortholog Gene Name | Species | GI # | % ID to HIO1002 | Score(s) (BLAST, Clustal, etc.) |
|---|---|---|---|---|
| One EST contig from potato | *Solarium tubersom* | gi|12588047<br>gi|15259347<br>consensus: SEQ ID NO: 7 | Length: 585<br>Identities: 0.653<br>Positives: 0.774<br>Frames: 3 | TBLASTN<br>Score: 691<br>Probability: 2.300000e−68 |
| One EST contig from sugar beet | *Beta vulgaris* | gi|26121630 | Length: 504<br>Identities: 0.667<br>Positives: 0.758<br>Frames: 1 | TBLASTN<br>Score: 577<br>Probability: 1.300000e−56 |
| One EST contig from soybean | *Glycine max* | gi|9205433<br>gi|12488109<br>gi|12773915<br>gi|15286042<br>gi|18731515<br>consensus: SEQ ID NO: 11 | Length: 605<br>Identities: 0.614<br>Positives: 0.733<br>Frames: 2 | TBLASTN<br>Score: 592<br>Probability: 1.500000e−57 |
| One EST contig from wheat | *Triticum aestivum* | gi|9742370<br>gi|20309688<br>gi|25194283<br>gi|25235692<br>gi|25237006<br>gi|25243036<br>gi|25261519 | Length: 1569<br>Identities: 0.638<br>Positives: 0.745<br>Frames: 1 | TBLASTN<br>Score: 992<br>Probability: 4.000000e−100 |

TABLE 3-continued

| Ortholog Gene Name | Species | GI # | % ID to HIO1002 | Score(s) (BLAST, Clustal, etc.) |
|---|---|---|---|---|
| | | gi\|25280706 gi\|25431065 gi\|25547029 gi\|25560875 gi\|32546080 gi\|32670437 consensus: SEQ ID NO: 13 | | |
| One EST contig from rice | Oryza sativa | gi\|5456487 gi\|13420908 gi\|700187 consensus: SEQ ID NO: 9 | Length: 463 Identities: 0.766 Positives: 0.901 Frames: 1 | TBLASTN Score: 469 Probability: 9.800000e−45 |
| One EST contig from poplar | Populus tremula | gi\|3857688 gi\|23959842 gi\|23960044 gi\|23963690 gi\|23997967 gi\|23998879 gi\|24062476 gi\|24065210 gi\|28609230 consensus: SEQ ID NO: 10 | Length: 1262 Identities: 0.674 Positives: 0.774 Frames: 2 | TBLASTN Score: 1040 Probability: 9.900000e−106 |
| One EST contig from tomato | Lycopersicon esculentum | gi\|5896833 gi\|5896833 gi\|5896833 gi\|12628275 gi\|12628275 gi\|12628275 gi\|16242572 consensus: SEQ ID NO: 8 | Length: 927 Identities: 0.652 Positives: 0.769 Frames: 2 | TBLASTN Score: 949 Probability: 3.600000e−106 |
| One EST contig from corn | Zea mays | gi\|5739680 gi\|21208932 gi\|407242 gi\|407243 consensus: SEQ ID NO: 12 | Length: 864 Identities: 0.626 Positives: 0.772 Frames: 3 | TBLASTN Score: 450 Probability: 3.000000e−50 |
| One EST contig from cotton | Gossypium hirsutum | gi\|3326250 | Length: 681 Identities: 0.629 Positives: 0.750 Frames: 1 | TBLASTN Score: 415 Probability: 8.600000e−40 |

Closest Plant Homologs:

| | | | | |
|---|---|---|---|---|
| At1g73650 | Arabidopsis thaliana | gi\|18410409 | Identities: 0.893 Positives: 0.893 Frames: N | BLASTP Score: 1351 P = 3.700000e−137 |
| At1g18180 | Arabidopsis thaliana | gi\|15221003 | Identities: 0.733 Positives: 0.806 Frames: N | BLASTP Score: 1122 P = 6.900000e−113 |
| gi\|13937298 | Oryza sativa | gi\|13937298 | Identities: 0.641 Positives: 0.760 Frames: N | BLASTP Score: 1004 P = 2.200000e−100 |
| gi\|31213708 | Anopheles gambiae | gi\|31213708 gi\|21299548 | Identities: 0.415 Positives: 0.588 Frames: N | BLASTP Score: 592 P = 1.000000e−56 |
| gi\|21355723 | Drosophila melanogaster | gi\|21355723 gi\|28574404 gi\|16648114 gi\|23093921 gi\|28380570 | Identities: 0.394 Positives: 0.564 Frames: N | BLASTP Score: 555 P = 8.300000e−53 |
| gi\|38105747 | Magnaporthe grisea70-15 | gi\|38105747 | Identities: 0.416 Positives: 0.549 Frames: N | BLASTP Score: 509 P = 6.300000e−48 |
| gi\|43807390 | environmental sequence | gi\|43807390 | Identities: 0.336 Positives: 0.529 Frames: N | BLASTP Score: 418 P = 2.700000e−38 |

This NCBI entry for At1g73650 (NP_849882.1) is a predicted trans-membrane protein. There are six predicted trans-membrane domains (predicted by TMHMM; amino acid residues 9-31; 64-86; 99-118; 138-155; 185-204; 209-231). The first trans-membrane domain overlaps with the signal anchor sequence (predicted by SignalP; probability=0.990; amino acid residues 1-28).

Psort2 predicts that At1g73650 may be localized to the endoplasmic reticulum, plasma membrane or the mitochondria (32% endoplasmic reticulum, 28% plasma membrane, 24% mitochondrial, 4% nuclear, 4% golgi apparatus, 4% vacuolar, 4% vesicles of secretory system by Psort2). However, At1g73650 is unlikely to be targeted to the mitochondria based on TargetP prediction.

Pfam analysis predicts that At1g73650 has one domain of unknown function (PF06966, amino acid residues 24-252):

| Model | Domain | seq-f* | seq-t | hmm-f | hmm-t | score | E-value |
|---|---|---|---|---|---|---|---|
| PF06966 | 1/1 | 24 | 252 .. | 1 | 266 [ ] | 453.0 | 4.9e−133 |

*Seq-f refers to "sequence-from" and seq-t refers to "sequence-to." The two periods following the seq-t number indicate that the matching region was within the sequence and did not extend to either end. The two brackets indicate that the match spanned the entire length of the profile HMM. hmm-f and hmm-t refer to the beginning and ending coordinates of the matching portion of the profile HMM.

Example 5

Transformed explants of rapeseed, soy, corn, sunflower, cotton, cocoa, safflower, oil palm, coconut palm, flax, castor and peanut are obtained through *Agrobacterium tumefaciens*-mediated transformation or microparticle bombardment. Plants are regenerated from transformed tissue. The greenhouse grown plants are then analyzed for the gene of interest expression levels as well as oil levels.

Example 6

This example provides analytical procedures to determine oil and protein content, mass differences, amino acid composition, free amino acid levels, and micronutrient content of transgenic maize plants.

Oil levels (on a mass basis and as a percent of tissue weight) of first generation single corn kernels and dissected germ and endosperm are determined by low-resolution $^1$H nuclear magnetic resonance (NMR) (Tiwari et al., *JAOCS*, 51:104-109 (1974); or Rubel, *JAOCS*, 71:1057-1062 (1994)), whereby NMR relaxation times of single kernel samples are measured, and oil levels are calculated based on regression analysis using a standard curve generated from analysis of corn kernels with varying oil levels as determined gravimetrically following accelerated solvent extraction. One-way analysis of variance and the Student's T-test (JMP, version 4.04, SAS Institute Inc., Cary, N.C., USA) are performed to identify significant differences between transgenic and non-transgenic kernels as determined by transgene-specific PCR.

Oil levels and protein levels in second generation seed are determined by NIT spectroscopy, whereby NIT spectra of pooled seed samples harvested from individual plants are measured, and oil and protein levels are calculated based on regression analysis using a standard curve generated from analysis of corn kernels with varying oil or protein levels, as determined gravimetrically following accelerated solvent extraction or elemental (% N) analysis, respectively. One-way analysis of variance and the Student's T-test are performed to identify significant differences in oil (% kernel weight) and protein (% kernel weight) between seed from marker positive and marker negative plants.

The levels of free amino acids are analyzed from each of the transgenic events using the following procedure. Seeds from each of the transgenic plants are crushed individually into a fine powder and approximately 50 mg of the resulting powder is transferred to a pre-weighed centrifuge tube. The exact sample weight is recorded and 1.0 ml of 5% trichloroacetic acid is added to each sample tube. The samples are mixed at room temperature by vortex and then centrifuged for 15 minutes at 14,000 rpm on an Eppendorf microcentrifuge (Model 5415C, Brinkmann Instrument, Westbury, N.Y.). An aliquot of the supernatant is removed and analyzed by HPLC (Agilent 1100) using the procedure set forth in Agilent Technical Publication "Amino Acid Analysis Using the Zorbax Eclipse-AAA Columns and the Agilent 1100 HPLC," Mar. 17, 2000.

Quantitative determination of total amino acids from corn is performed by the following method. Kernels are ground and approximately 60 mg of the resulting meal is acid-hydrolyzed using 6 N HCl under reflux at 100° C. for 24 hrs. Samples are dried and reconstituted in 0.1 N HCl followed by precolumn derivatization with α-phthalaldehyde (OPA0 for HPLC analysis. The amino acids are separated by a reverse-phase Zorbax Eclipse XDB-C18 HPLC column on an Agilent 1100 HPLC (Agilent, Palo Alto, Calif.). The amino acids are detected by fluorescence. Cysteine, proline, asparagine, glutamine, and tryptophan are not included in this amino acid screen (Henderson et al., "Rapid, Accurate, Sensitive and Reproducible HPLC Analysis of Amino acids, Amino Acid Analysis Using Zorbax Eclipse-AAA Columns and the Agilent 1100 HPLC," Agilent Publication (2000); see, also, "Measurement of Acid-Stable Amino Acids," AACC Method 07-01 (American Association of Cereal Chemists, Approved Methods, 9th edition (LCCC# 95-75308)). Total tryptophan is measured in corn kernels using an alkaline hydrolysis method as described (Approved Methods of the American Association of Cereal Chemists-10$^{th}$ edition, AACC ed, (2000) 07-20 Measurement of Tryptophan-Alakline Hydrolysis).

Tocopherol and tocotrienol levels in seeds are assayed by methods well-known in the art. Briefly, 10 mg of seed tissue are added to 1 g of microbeads (Biospec Product Inc, Barlesville, Okla.) in a sterile microfuge tube to which 500 μl 1% pyrogallol (Sigma Chemical Co., St. Louis, Mo.)/ethanol have been added. The mixture is shaken for 3 minutes in a mini Beadbeater (Biospec) on "fast" speed, then filtered through a 0.2 μm filter into an autosampler tube. The filtered extracts are analyzed by HPLC using a Zorbax silica HPLC column (4.6 mm×250 mm) with a fluorescent detection, an excitation at 290 nm, an emission at 336 nm, and bandpass and slits. Solvent composition and running conditions are as listed below with solvent A as hexane and solvent B as methyl-t-butyl ether. The injection volume is 20 µl, the flow rate is 1.5 ml/minute and the run time is 12 minutes at 40° C. The solvent gradient is 90% solvent A, 10% solvent B for 10 minutes; 25% solvent A, 75% solvent B for 11 minutes; and 90% solvent A, 10% solvent B for 12 minutes. Tocopherol standards in 1% pyrogallol/ethanol are run for comparison (α-tocopherol, γ-tocopherol, β-tocopherol, δ-tocopherol, and tocopherol (tocol)). Standard curves for alpha, beta, delta, and gamma tocopherol are calculated using Chemstation software (Hewlett Packard). Tocotrienol standards in 1% pyrogallol/ethanol are run for comparison (α-tocotrienol, γ-tocotrienol, β-tocotrienol, δ-tocotrienol). Standard curves for α-, β-, δ-, and γ-tocotrienol are calculated using Chemstation software (Hewlett Packard).

Carotenoid levels within transgenic corn kernels are determined by a standard protocol (Craft, *Meth. Enzymol.*, 213: 185-205 (1992)). Plastiquinols and phylloquinones are determined by standard protocols (Threlfall et al., *Methods in Enzymology*, XVIII, part C, 369-396 (1971); and Ramadan et al., *Eur. Food Res. Technol.*, 214(6):521-527 (2002)).

REFERENCES

Altschul, S. F. et al., J. Mol. Biol. 215:403-410, 1990.
Altschul, S. F. et al., Nucleic Acids Res. 25:3389-3402, 1997.
Ausubel F M et al., Current Protocols in Molecular Biology, John Wiley & Sons, New York, N.Y., 1993.
Baldwin D et al., Cur Opin Plant Biol. 2(2):96-103, 1999.
Bateman et al., 1999, Nucleic Acids Res 27:260-262 (website at pfam.wustl.edu).
Baulcombe D, Arch Virol Suppl 15:189-201, 1999.
Cannon et al., Plant Molec. Biol. (1990) 15:39-47.
Ch'ng et al., Proc. Natl. Acad. Sci. USA (1989) 86:10006-10010
Christensen S et al., 9*th* International Conference on *Arabidopsis* Research. Univ. of Wisconsin-Madison, Jun. 24-28, 1998. Abstract 165.
Christou et al., Proc. Natl. Acad. Sci USA (1989) 86:7500-7504.
De Block et al., Plant Physiol. (1989) 91:694-701.
Dieffenbach C and Dveksler G (Eds.) PCR Primer: A Laboratory Manual, Cold Spring Harbor Laboratory Press, NY, 1989.
Everett et al., Bio/Technology (1987) 5:1201
Feldmann et al., Science 243: 1351-1354, 1989.
Focks N and Benning C, Plant Physiol 118:91-101, 1998.
Fridborg I et al., Plant Cell 11: 1019-1032, 1999.
Harlow E and Lane D, Antibodies: A Laboratory Manual, Cold Spring Harbor Laboratory Press, 1988, New York.
Harlow E and Lane D, Using Antibodies: A Laboratory Manual, Cold Spring Harbor Laboratory Press, 1999, New York
Hayashi H et al., Science 258: 1350-1353, 1992.
Jako et al., Plant Physiology 126(2):861-74, 2001.
James D W and Dooner HK (1990) Theor Appl Genet 80, 241-245.
Jones J D et al., Transgenic Res 1:285-297 1992.
Kardailsky I et al., Science 286: 1962-1965, 1999.
Katavic V et al., Plant Physiology 108(1):399-409, 1995.
Kline et al., Nature (1987) 327:70.
Kunkel T A et al., Methods Enzymol. 204:125-39, 1991.
Lemieux B., et al., 1990, Theor Appl Genet 80, 234-240.
Nakamura Y et al., 1999, Nucleic Acids Res 27:292.
Napoli, et al., Plant Cell 2:279-289, 1990.
Okuley et al., Plant Cell 6(1):147-158, 1994.
Sambrook et al., Molecular Cloning: A Laboratory Manual (Second Edition), Cold Spring Harbor Press, Plainview, N.Y., 1989.
Schaffer R, et al., Cell 93: 1219-1229, 1998.
Sheehy et al., Proc. Natl. Acad. Sci. USA (1988) 85:8805-8809.
Smith, et al., Nature 334:724-726, 1988.
Smith et al., Mol. Gen. Genetics (1990) 224:477-481.
Thompson J D et al., Nucleic Acids Res 22:4673-4680, 1994.
van der Krol et al., Biotechniques (1988) 6:958-976.
van der Krol et al., The Plant Cell (1990) 2:291-299.
Van Haaren M J J et al., Plant Mol Bio 21:625-640, 1993.
Verdaguer B et al., Plant Mol Biol 37:1055-1067, 1998.
Waterhouse, et al., Proc. Natl. Acad. Sci. USA 95:13959-13964, 1998.
Weigel D, et al., Plant Physiology, 122:1003-1013, 2000.
Wilson K et al., Plant Cell 8: 659-671, 1996.
Yadav N S et al., (1993) Plant Physiol 103, 467-476.

The invention claimed is:

1. A method of producing oil comprising growing a transgenic plant comprising a plant transformation vector comprising a nucleotide sequence that encodes a HIO1002 polypeptide comprising an amino acid sequence having at least 95% sequence identity to the amino acid sequence of SEQ ID NO: 2, whereby the transgenic plant has a high oil phenotype relative to a plant of the same species not comprising the plant transformation vector; and recovering oil from said transgenic plant.

2. The method of claim 1, wherein the oil is recovered from a seed of the plant, wherein said seed comprises said plant transformation vector.

3. A method of producing a plant with a high oil phenotype, said method comprising:
   a) introducing into progenitor cells of the plant a plant transformation vector comprising a heterologous constitutive promoter operatively linked to a nucleotide sequence that encodes a HIO1002 polypeptide comprising an amino acid sequence having at least 95% sequence identity to the amino acid sequence of SEQ ID NO:2, to produce transformed cells overexpressing the polypeptide;
   b) growing the transformed progenitor cells to produce a transgenic plant, wherein said polynucleotide sequence is expressed; and
   c) identifying said transgenic plant that exhibits a high oil phenotype relative to a plant of the same species not comprising the plant transformation vector.

4. The method of claim 1, wherein the nucleotide sequence encodes a HIO1002 polypeptide consisting of an amino acid sequence having at least 95% sequence identity to the amino acid sequence of SEQ ID NO: 2.

5. The method of claim 1, wherein the nucleotide sequence encodes a HIO1002 polypeptide comprising the amino acid sequence set forth as SEQ ID NO: 2.

6. The method of claim 1, wherein the nucleotide sequence encodes a HIO1002 polypeptide consisting of the amino acid sequence set forth as SEQ ID NO: 2.

7. The method of claim 3, wherein the nucleotide sequence encodes a HIO1002 polypeptide consisting of an amino acid sequence having at least 95% sequence identity to the amino acid sequence of SEQ ID NO: 2.

8. The method of claim 3, wherein the nucleotide sequence encodes a HIO1002 polypeptide comprising the amino acid sequence set forth as SEQ ID NO: 2.

9. The method of claim 3, wherein the nucleotide sequence encodes a HIO1002 polypeptide consisting of the amino acid sequence set forth as SEQ ID NO: 2.

* * * * *

SEQUENCE LISTING

```
<160> NUMBER OF SEQ ID NOS: 13

<210> SEQ ID NO 1
<211> LENGTH: 1272
<212> TYPE: DNA
<213> ORGANISM: Arabidopsis thaliana

<400> SEQUENCE: 1
ttaaagtaat gactttttt  tatatgatat  attctcaatt  ttgttactcg  gaaacaatag      60
aaaggataac gaatcgtttc  tcttcgatcg  aaagaatata  tatttggaag  ttttctctgc     120 tttttgttt  tcgtttgata  gaatgggaac  agttctcgat  tcgcattttc  tggctctcac     180
tgctattgtc actgtgattt  accagttcat  attcttcgta  atcacggctc  ttttcaaatt     240
tgatcaagtc actgactttg  ctggtagcac  aaacttcgtt  atacttgctg  tgttaacact     300
tgttctcaaa gcctcttggc  attttcgaca  gatagtattg  actttgctag  ttgtggtatg     360
```

```
gggtcttcgc ttggggattt tccttctaat gaggatcttg caatgggggg aagatcgtcg    420
ctttgatgaa cagcgtggaa atatagtgag actaatcatt ttctggactc ttcaggctgt    480
gtgggtttgg acggttagct tacctttaac acttgttaat gcaagtgatg gtggtggatc    540
tcttaaaccc gcagatgtta tcggttggac tatgtgggtt ttcggtttct tgattgaagc    600
tgcagctgat caacagaagc tatcattcaa aaactctcct gaaaacagag gaaaatggtg    660
tgatgttgga gtctggaagt attcaagaca tccaaactac ttcggtgaga tgttactgtg    720
gtggggaatc tttgtggctg catcgcctgt gcttgaaggt gcagagtatc ttgtcatatt    780
cggaccactc tttctcactt tgctacttct attcgtcagc ggcataccat tactcgaggc    840
atcggctgac aaaaaacatg gaaactcagg agcttacaga tcctacaaga agacaacaag    900
tcctctgatt ctgttcccaa gaggagtgta tgggaactta ccaggatggt tcaagacggt    960
ctttctcttc gagtttccat tttacagccg aaatctccct caagaggtgg ctgtttagta   1020
actgcttatt ctgtttcagt ttcatctttt atatcttact ttagtgtttg atgagtttgg   1080
cttctctttg ttgtatgtgt gcaagaaagt tagggtagac tccaaaacag caaagagaaa   1140
gaagtaaaag atgactgatt tgtgatactc atatttgagt tattgttctt cacaacactc   1200
tttgataaaa tttgtgtaaa aaattgcccg taagaaactg aatttgtttg aaatattgga   1260
cagtcttgac ag                                                       1272
```

```
<210> SEQ ID NO 2
<211> LENGTH: 291
<212> TYPE: PRT
<213> ORGANISM: Arabidopsis thaliana

<400> SEQUENCE: 2

Met Gly Thr Val Leu Asp Ser His Phe Leu Ala Leu Thr Ala Ile Val
1               5                   10                  15

Thr Val Ile Tyr Gln Phe Ile Phe Phe Val Ile Thr Ala Leu Phe Lys
            20                  25                  30

Phe Asp Gln Val Thr Asp Phe Ala Gly Ser Thr Asn Phe Val Ile Leu
        35                  40                  45

Ala Val Leu Thr Leu Val Leu Lys Ala Ser Trp His Phe Arg Gln Ile
    50                  55                  60

Val Leu Thr Leu Val Val Val Trp Gly Leu Arg Leu Gly Ile Phe
65                  70                  75                  80

Leu Leu Met Arg Ile Leu Gln Trp Gly Glu Asp Arg Arg Phe Asp Glu
                85                  90                  95

Gln Arg Gly Asn Ile Val Arg Leu Ile Ile Phe Trp Thr Leu Gln Ala
            100                 105                 110

Val Trp Val Trp Thr Val Ser Leu Pro Leu Thr Leu Val Asn Ala Ser
        115                 120                 125

Asp Gly Gly Ser Leu Lys Pro Ala Asp Val Ile Gly Trp Thr Met
    130                 135                 140

Trp Val Phe Gly Phe Leu Ile Glu Ala Ala Asp Gln Gln Lys Leu
145                 150                 155                 160

Ser Phe Lys Asn Ser Pro Glu Asn Arg Gly Lys Trp Cys Asp Val Gly
                165                 170                 175

Val Trp Lys Tyr Ser Arg His Pro Asn Tyr Phe Gly Glu Met Leu Leu
            180                 185                 190

Trp Trp Gly Ile Phe Val Ala Ala Ser Pro Val Leu Glu Gly Ala Glu
        195                 200                 205
```

```
Tyr Leu Val Ile Phe Gly Pro Leu Phe Leu Thr Leu Leu Leu Phe
    210                 215                 220

Val Ser Gly Ile Pro Leu Leu Glu Ala Ser Ala Asp Lys Lys His Gly
225                 230                 235                 240

Asn Ser Gly Ala Tyr Arg Ser Tyr Lys Lys Thr Thr Ser Pro Leu Ile
                245                 250                 255

Leu Phe Pro Arg Gly Val Tyr Gly Asn Leu Pro Gly Trp Phe Lys Thr
            260                 265                 270

Val Phe Leu Phe Glu Phe Pro Phe Tyr Ser Arg Asn Leu Pro Gln Glu
        275                 280                 285

Val Ala Val
    290

<210> SEQ ID NO 3
<211> LENGTH: 1192
<212> TYPE: DNA
<213> ORGANISM: Arabidopsis thaliana

<400> SEQUENCE: 3
ttaaagtaat gactttttt tatatgatat attctcaatt ttgttactcg gaaacaatag      60
aaaggataac gaatcgtttc tcttcgatcg aaagaatata tatttggaag ttttctctgc    120 tttttgttt tcgtttgata gaatgggaac agttctcgat tcgcattttc tggctctcac    180
tgctattgtc actgtgattt accagttcat attcttcgta atcacggctc ttttcaaatt    240
tgatcaagtc actgactttg ctggtagcac aaacttcgtt atacttgctg tgttaacact    300
tgttctcaaa gcctcttggc atttctgaca gatagtattg actttgctag ttgtggtatg    360
gggtcttcgc ttggggattt tccttctaat gaggatcttg caatgggggg aagatcgtcg    420
ctttgatgaa cagcgtggaa atatagtgag actaatcatt ttctggactc ttcaggctgt    480 gtgggttttgg acggttagct tacctttaac acttgttaat gcaagtgatg gtggtggatc    540
tcttaaaccc gcagatgtta tcggttggac tatgtgggtt ttcggtttct tgattgaagc    600
tgcagctgat caacagaagc tatcattcaa aaactctcct gaaaacagag gaaaatggtg    660
tgatgttgga gtctggaagt attcaagaca tccaaactac ttcggtgaga tgttactgtg    720
gtggggaatc tttgtggctg catcgcctgt gcttgaaggt gcagagtatc ttgtcatatt    780
cggaccactc tttctcactt tgctacttct attcgtcagc ggcataccat tactcgaggc    840
atcggctgac aaaaaacatg gaaactcagg agcttacaga tcctacaaga agacaacaag    900
tcctctgatt ctgttcccaa gaggagtgta tgggaactta ccaggatggt tcaagacggt    960
ctttctcttc gagtttccat tttacagccg aaatctccct caagagttag ggtagactcc   1020
aaaacagcaa agagaaagaa gtaaagatg actgatttgt gatactcata tttgagttat   1080
tgttcttcac aacactcttt gataaaattt gtgtaaaaaa ttgcccgtaa gaaactgaat   1140
ttgtttgaaa tattggacag tcttgacaga ttatctcagt gtatttggt tc            1192

<210> SEQ ID NO 4
<211> LENGTH: 290
<212> TYPE: PRT
<213> ORGANISM: Arabidopsis thaliana

<400> SEQUENCE: 4

Met Gly Thr Val Leu Asp Ser His Phe Leu Ala Leu Thr Ala Ile Val
1               5                   10                  15

Thr Val Ile Tyr Gln Phe Ile Phe Phe Val Ile Thr Ala Leu Phe Lys
            20                  25                  30
```

Phe Asp Gln Val Thr Asp Phe Ala Gly Ser Thr Asn Phe Val Ile Leu
            35                  40                  45

Ala Val Leu Thr Leu Val Leu Lys Ala Ser Trp His Phe Arg Gln Ile
 50                  55                  60

Val Leu Thr Leu Leu Val Val Trp Gly Leu Arg Leu Gly Ile Phe
 65                  70                  75                  80

Leu Leu Met Arg Ile Leu Gln Trp Gly Glu Asp Arg Arg Phe Asp Glu
                85                  90                  95

Gln Arg Gly Asn Ile Val Arg Leu Ile Ile Phe Trp Thr Leu Gln Ala
            100                 105                 110

Val Trp Val Trp Thr Val Ser Leu Pro Leu Thr Leu Val Asn Ala Ser
            115                 120                 125

Asp Gly Gly Gly Ser Leu Lys Pro Ala Asp Val Ile Gly Trp Thr Met
130                 135                 140

Trp Val Phe Gly Phe Leu Ile Glu Ala Ala Asp Gln Gln Lys Leu
145                 150                 155                 160

Ser Phe Lys Asn Ser Pro Glu Asn Arg Gly Lys Trp Cys Asp Val Gly
                165                 170                 175

Val Trp Lys Tyr Ser Arg His Pro Asn Tyr Phe Gly Glu Met Leu Leu
            180                 185                 190

Trp Trp Gly Ile Phe Val Ala Ala Ser Pro Val Leu Glu Gly Ala Glu
            195                 200                 205

Tyr Leu Val Ile Phe Gly Pro Leu Phe Leu Thr Leu Leu Leu Phe
 210                 215                 220

Val Ser Gly Ile Pro Leu Leu Glu Ala Ser Ala Asp Lys Lys His Gly
225                 230                 235                 240

Asn Ser Gly Ala Tyr Arg Ser Tyr Lys Lys Thr Ser Pro Leu Ile
                245                 250                 255

Leu Phe Pro Arg Gly Val Tyr Gly Asn Leu Pro Gly Trp Phe Lys Thr
            260                 265                 270

Val Phe Leu Phe Glu Phe Pro Phe Tyr Ser Arg Asn Leu Pro Gln Glu
            275                 280                 285

Leu Gly
    290

<210> SEQ ID NO 5
<211> LENGTH: 1337
<212> TYPE: DNA
<213> ORGANISM: Arabidopsis thaliana

<400> SEQUENCE: 5
ttaaagtaat gactttttt tatatgatat attctcaatt ttgttactcg gaaacaatag      60
aaaggataac gaatcgtttc tcttcgatcg aaagaatata tatttggaag ttttctctgc    120 tttttgttt tcgtttgata gaatgggaac agttctcgat tcgcattttc tggctctcac    180
tgctattgtc actgtgattt accagttcat attcttcgta atcacggctc ttttcaaatt    240
tgatcaagtc actgactttg ctggtagcac aaacttcgtt atacttgctg tgttaacact    300
tgttctcaaa gcctcttggc attttcgaca gatagtattg actttgctag ttgtggtatg    360
gggtcttcgc ttggggattt tccttctaat gaggatcttg caatgggggg aagatcgtcg    420
ctttgatgaa cagcgtggaa atatagtgag actaatcatt ttctggactc ttcaggctgt    480
gtgggtttgg acggttagct tacctttaac acttgttaat gcaagtgatg gtggtggatc    540
tcttaaaccc gcagatgtta tcggttggac tatgtgggtt ttcggtttct tgattgaagc    600

```
tgcagctgat caacagaagc tatcattcaa aaactctcct gaaaacagag gaaaatggtg    660
tgatgttgga gtctggaagt attcaagaca tccaaactac ttcggtgaga tgttactgtg    720
gtggggaatc tttgtggctg catcgcctgt gcttgaaggt gcagagtatc ttgtcatatt    780
cggaccactc tttctcactt tgctacttct attcgtcagc ggcataccat tactcgaggc    840
atcggctgac aaaaaacatg gaaactcagg agcttacaga tcctacaaga agacaacaag    900
tcctctgatt ctgttcccaa gaggagtgta tgggaactta ccaggatggt tcaagacggt    960
ctttctcttc gagtttccat tttacagccg aaatctccct caagagggta gactccaaaa    1020
cagcaaagag aaagaagtaa aagatgactg atttgtgata ctcatatttg agttattgtt    1080
cttcacaaca ctctttgata aaatttgtgt aaaaaattgc ccgtaagaaa ctgaatttgt    1140
ttgaaatatt ggacagtctt gacagattat ctcagttgta tttggttctt tttttatgt    1200 gattttgttt tttggttaaa aaagttccc attccaagaa tcgaacccgg gtctcctggg    1260
tgaaagccaa atatcctaac cgctggacga catcggattt gattatttga ttatttaatt    1320
actttatatg ttgattt    1337
```

<210> SEQ ID NO 6
<211> LENGTH: 302
<212> TYPE: PRT
<213> ORGANISM: Arabidopsis thaliana

<400> SEQUENCE: 6

```
Met Gly Thr Val Leu Asp Ser His Phe Leu Ala Leu Thr Ala Ile Val
1               5                   10                  15

Thr Val Ile Tyr Gln Phe Ile Phe Phe Val Ile Thr Ala Leu Phe Lys
            20                  25                  30

Phe Asp Gln Val Thr Asp Phe Ala Gly Ser Thr Asn Phe Val Ile Leu
        35                  40                  45

Ala Val Leu Thr Leu Val Leu Lys Ala Ser Trp His Phe Arg Gln Ile
    50                  55                  60

Val Leu Thr Leu Leu Val Val Trp Gly Leu Arg Leu Gly Ile Phe
65                  70                  75                  80

Leu Leu Met Arg Ile Leu Gln Trp Gly Glu Asp Arg Arg Phe Asp Glu
                85                  90                  95

Gln Arg Gly Asn Ile Val Arg Leu Ile Ile Phe Trp Thr Leu Gln Ala
            100                 105                 110

Val Trp Val Trp Thr Val Ser Leu Pro Leu Thr Leu Val Asn Ala Ser
        115                 120                 125

Asp Gly Gly Ser Leu Lys Pro Ala Asp Val Ile Gly Trp Thr Met
    130                 135                 140

Trp Val Phe Gly Phe Leu Ile Glu Ala Ala Asp Gln Gln Lys Leu
145                 150                 155                 160

Ser Phe Lys Asn Ser Pro Glu Asn Arg Gly Lys Trp Cys Asp Val Gly
                165                 170                 175

Val Trp Lys Tyr Ser Arg His Pro Asn Tyr Phe Gly Glu Met Leu Leu
            180                 185                 190

Trp Trp Gly Ile Phe Val Ala Ala Ser Pro Val Leu Glu Gly Ala Glu
        195                 200                 205

Tyr Leu Val Ile Phe Gly Pro Leu Phe Leu Thr Leu Leu Leu Leu Phe
    210                 215                 220

Val Ser Gly Ile Pro Leu Leu Glu Ala Ser Ala Asp Lys Lys His Gly
225                 230                 235                 240
```

```
Asn Ser Gly Ala Tyr Arg Ser Tyr Lys Lys Thr Thr Ser Pro Leu Ile
            245                 250                 255

Leu Phe Pro Arg Gly Val Tyr Gly Asn Leu Pro Gly Trp Phe Lys Thr
        260                 265                 270

Val Phe Leu Phe Glu Phe Pro Phe Tyr Ser Arg Asn Leu Pro Gln Glu
            275                 280                 285

Gly Arg Leu Gln Asn Ser Lys Glu Lys Glu Val Lys Asp Asp
        290                 295                 300

<210> SEQ ID NO 7
<211> LENGTH: 585
<212> TYPE: DNA
<213> ORGANISM: Artificial sequence
<220> FEATURE:
<223> OTHER INFORMATION: synthetic construct

<400> SEQUENCE: 7
gcaaagaccg aacagggaaa gttatggatt cccatttctt gggcctcact gccattgtta      60
ccttgggtta tcagttaaca ttttttcatta tcacagcact cttcaggttt gataaagtta    120
ctgactttgc gggaggtacg aacttcatta tacttgctat tttgaccttg gtgctaaagg    180
gttcatggca ctttcgacag gtggttttgt ctctatttgt agttatatgg gccttcggt     240 tggggctttt cttattaatg aggatattac agtgggggga ggacagacgt tttgatgaca    300
aacgtgacaa tcttggaaaa ctggcaatat tttggatact tcaggcaatc tgggtatgga    360
ctgttagttt accagtgaca gttgttaatg caagtgacaa gcagccttct gttcaggctc    420
aagacatcat tggttggatt atgtggatta ttgggatttt agttgagatt acagctgacc    480
aacaaaaatt ggcgttcaaa aactcctcgg agaacagagg aaagtggtgc agtgttggcc    540
tttggaaata ttctcgtcat ccaaactatt tggtgagat tttac                     585

<210> SEQ ID NO 8
<211> LENGTH: 927
<212> TYPE: DNA
<213> ORGANISM: Artificial sequence
<220> FEATURE:
<223> OTHER INFORMATION: synthetic construct

<400> SEQUENCE: 8
ttctttgtga atggggacag ttatagactc ccatttgttg ggcctaaccg ccattgttac      60
agtggtttac caattaatct ttttataat cacagcactc ctcaaatttg ataaagtcac     120
agatttctca ggaggtacaa atttcattgt gcttgcagaa ttaactttga tactaaaagg    180
ttcatggaat tttcgacagg tggttttgtc tgtgtttgtc gtgatatggg ccttcgact     240 ggggctattt ctattaatga ggatattaca atggggcgag atagacgtt tgatgataa     300 gcgtgataat ctggggaaac tggcaatatt tggctattt caggcaatct gggtgtggac    360
tgtgagttta ccagtgacag ttgttaatgc aagtgaccac caaccatctg ttcagacggt    420
agacatcatt ggttggatta tgtggtctat cggaatatca gttgagatta cagctgacca    480
acaaaaattg gcattcaaaa actccccgga aaacagagga agtggtgca gtgatggcct    540 ttggaaatat tctcgccatc caaactattt ggtgagatt tactttggt ggggaatttt     600 cctggcttcc acaccggtgc tagagggtgc tgaatggctg gttgtgtttg gaccagtctt    660
cataaccttg ctgctccttt tgttagtgg catacccttg cttgaggcat caggagacaa    720
gaagtttgga aatgttggtg catacagatc atataagaga aaaactagcc ctcttattct    780
```

-continued

| gctgcctcct ggtgtgtatg gggagtcttc ctcaatggtt caaaaccata ctccttttttg | 840 |
| agtttccttt ttacagtcgc aatcttccgc agaaaagagt aagctggaaa tagacaaccc | 900 |
| agccaggaag cagtagaaca gacccga | 927 |

<210> SEQ ID NO 9
<211> LENGTH: 465
<212> TYPE: DNA
<213> ORGANISM: Artificial sequence
<220> FEATURE:
<223> OTHER INFORMATION: synthetic construct
<220> FEATURE:
<221> NAME/KEY: misc_feature
<222> LOCATION: (413)..(413)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t

<400> SEQUENCE: 9

| gtgagaggag gaggataaac ggaggaggcc gcgatgggaa ccgtgctgga ctcccacttc | 60 |
| ctggcgctca cggccatcgt cactgtggga tatcagctgg tgttcttcat catcaccgcg | 120 |
| ctcctgcggt tcgataaagt cactgatttc gcaggaagta cgaatttcat catacttgca | 180 |
| atcctcacgc tagctttgaa gggagcatgg catttccgtc aggttgtatt gactgtgctc | 240 |
| gttgtgattt ggggtcttcg cttaggacta ttcttattaa tgaggattct tcaatgggga | 300 |
| gaggacaaac ggtttgatga atgcgcgat aacttgggaa actagcagt tttctggatt | 360 |
| ttccaggctg tttggggtat ggactggtcc agcttgcctg gttacaattg tgnacgcaag | 420 |
| tggccagcga tccctccaat tgaagcccgt gatatnattg gttgg | 465 |

<210> SEQ ID NO 10
<211> LENGTH: 1262
<212> TYPE: DNA
<213> ORGANISM: Artificial sequence
<220> FEATURE:
<223> OTHER INFORMATION: synthetic construct

<400> SEQUENCE: 10

| aagagaaaat aaaagaagag acaccccata aggccataag cataaaagga gctgacaaat | 60 |
| gaacacaaca aactgaaaaa atcagtcttt atagatcgaa caaaactata gtgaagtaca | 120 |
| acgtaatccc ctcaaaatgg gaaccgtttt agactcccat tttctagcac tcactgccat | 180 |
| cgtcactgtg ggataccaac tgctgttttt cgttatcact gcccttctga gtttgataaa | 240 |
| agtcactgac tttgccggaa gcacaaattt tattatacta gctgtgttga ctctggtttt | 300 |
| gaaagggaca tggcatttca gacaggtagt cttaagtttc cttgtagtat cttggggtct | 360 |
| tcgcctggga ctgttcctgt tactgaggat tctgcagtgg ggggaggata gacgttttga | 420 |
| tgaaatgcgt agtaacttgg ggaaattagc tgttttctgg atatttcagg ctgtctgggt | 480 |
| gtggactgtg agtttaccctg taacagtggt taatggaatt gacagggatc cttccgttca | 540 |
| ggctgcagac ataattggct ggattatgtg gtctgttggt gtttcagttg aagctacagc | 600 |
| tgatcaacaa aaactgacat tcaagaatgc tccacaaaac agagggaaat ggggcaatgt | 660 |
| tggattatgg aatatatctc gtcacccaaa ctattttggc gaaattctcc tttggtgggg | 720 |
| tattttttgtg gcttctgcac ctgtactgga aggtgctgaa tggctggtga tccttgggcc | 780 |
| aatcttttctc acattgttgc ttcttttttgt cagtggcata ccattgcttg agcaatctgc | 840 |
| tgacaagaaa tttggcaacg tggctgcata cagggcatat aaaaggacaa ccagccctct | 900 |

```
aattccactg ccccaagcag tgtacaggag cttaccttca tggttcaaaa ctgttttcct    960 cttttgaattt cctctctaca gtcgtaattt ccagaagag gggtcaacat gaacaagaca   1020
aggtggaggc agcgatggat cgaagattgg ctagaagttc aacagggaa tctgccctgt    1080 tttggtaact ttaatgtact aggaatagtt ttagctgtta agctacatag acgccatgtt   1140
ctttctatta ctagctgtcg gttgattttc tttctcctgc ctgaaacatg tctccacctc   1200
tactgttctg tccactgagt ttccttccca cacaatcaat gctgattct tatatttaag    1260 tt                                                                   1262

<210> SEQ ID NO 11
<211> LENGTH: 605
<212> TYPE: DNA
<213> ORGANISM: Artificial sequence
<220> FEATURE:
<223> OTHER INFORMATION: synthetic construct

<400> SEQUENCE: 11
gtttatccaa cgaggtctgt tttattattg caagagttaa gaactcgact caagaagaca    60
gcaaaagtac tgagccatgg gtaccgtcat cgagtcccat ttcttagcct tcactgccct   120
tgtcactatt gcctatcagt ttctgttttt cgtcgtcact gcgctcctca aattcgacaa   180
agtcactgat tttgctggaa gtacgaattt catcataatt gctgcattga ccctggtcat   240
caaagcctcc tggtattttc gacagataat cctcactttg tttgttggga catggggact   300
tcgcctctgc cttttcctcc tattcagaat tttgcagtgg ggagaggacc ggcgcttcga   360
tgaaatgcgt agtaatttgg gtagactggc catattttgg atatttcagg ctgtctgggt   420
gtgggttgtg agtttacctg ttacgttggt taatgcaagc gacagaaatc ccttcctaca   480
ggttgttgat atagtagggt ggattttgtg ggctgtgggt tttattgtgg aaggtacagc   540
agatcaacaa aagctgcatt tcaaaagatc ttcagaaaat agagggaagt ggtgtaatgt   600
tggac                                                                605

<210> SEQ ID NO 12
<211> LENGTH: 864
<212> TYPE: DNA
<213> ORGANISM: Artificial sequence
<220> FEATURE:
<223> OTHER INFORMATION: synthetic construct

<400> SEQUENCE: 12
gcacgagcag aaacccctcg attgaagcca gggatataat cggttggata atatggttgg    60
tcgggatatg tgtagaagca acagctgatc agcagaagct tgtgttcaaa aattctccaa   120
gtaacagggg aaagtggtgc aacgccggtc tttggaagta ctctcgccac ccgaactact   180
ttggggagat attcctttgg tggggagtat tgtagcatc gaccccagtt atctcagatg    240
ccgaatggct tgtgattctt ggacctatat tcctgactct tctgcttctt ttcgttagtg   300
gaatcccact cctcgagtca tctgctgata agcgctatgg acgattggag gaataccgtg   360
catacaagaa cactacaagc cctcttatcc catgccacct gctgtgtatg gttccctgcc   420
tgcgtggttc aaggttgcct tcctccttga gctcccgctc tacaatcctg gccggggagg   480
tgatccaatc aaaccagaat gagcccattg atgggtcagc ctgatgttta tgttgctatt   540
gtgtgcgtgg cagttattcc accttcgatt ccaaggggtt acagtggagt ttggcccctg   600
atttatcgct cgcgaggctc aaacatgtat cttgttggtg gaaagttaga tttctttgt    660
```

```
tgccctccct gcctccatgt gcagatgaat agatgcttag aaacctgaac gtggaacgtg      720
ttcaccttcc tcgctccaaa aaagtgggaa cggaacaatc ttgtccatat agtgttaaag      780 tattttttt taagtacggt accacgttcc tgtttctggt tcccatcaat ccgagaactg       840
attagatgat caaaaaactc gtgc                                             864

<210> SEQ ID NO 13
<211> LENGTH: 1569
<212> TYPE: DNA
<213> ORGANISM: Artificial sequence
<220> FEATURE:
<223> OTHER INFORMATION: synthetic construct

<400> SEQUENCE: 13
gcacgaggag gcgatcgcac cacggtcccg tctcgcacag ccgcgcattc gcaccaccag       60
ggtcgcatcg cacgcattcg cccgcctccc tgtccagcct ccagccacaa gtgacaactg      120
acaagtcctc ctgacctcct cccctccca acgcgctccg ccgggtcgca tcgccgccgc      180
cgccgccgtc gaccgaaccc agtccaaccc ccgttaaaag cccggccggc gcgcgtgctc      240
gcttctcact tcattttaat tctcaaagaa aggaaaggga gaaggataaa gaaacagacc      300
aacaaatcca ctgacggccg gcggggaaga aaaggcgaga agatgggaac agtgctggac      360
tcccacttcc tggcgctcac cgccctcgtc accgtcgggt accagctggt gttcttcatc      420
atcacagccc tcctccgctt cgacaaggtc acggatttcg caggcagtac aaattttgtc      480
ataatcgccg tcctggtagc agctttgaag ggaacatggc acttccgtca gatcgtgttg      540
acagtgcttg ttataatctg gggacttcgt ctggcagtgt ttttactaat gaggattttg      600
caatggggag aggacaaacg gtttgatgag atgcgcagta acttgggaaa attagctgtc      660
ttctggactt ttcaggctgt ctgggtttgg actgtcagct tgcctgttac aattgtgaac      720
gcaagtagca gaaaccttc tattgaagct cgggatatca ttggttggat aatgtgggtc      780
atcgggctat ctgtggaagc tatagctgat cagcaaaagc ttaaattcaa gaactctcca      840 agcaatagg gaaagtggtg taatgtgggc ctttggagtt atactcggca cccaaattac      900
tttggggaga tgttcctttg gtgggggtg tttgtagcat caaccccggt tctctcagga      960
gctgaatggc ttgtaatctt ggggcccatc ttcctgacgc tcttgcttct tttcgttagt     1020
gggatcccac ttcttgagtc atctgctgat aagcgctttg gtcggtctga ggaataccgc     1080
acatacaaga aaaccacaag ccctcttatc ccattgccgc cggtcgtgta tggagccctg     1140
cccgattggt tcaaggtggc attcctcctg gagctgcccc tctacaaccc cggaccggaa     1200
cgcgaccccg tcagctgagt gatgaatgtg cattgttctt ctgatcacaa gtgattatac     1260
atgtaatgta ctgcttttat tctggatggg tgattctttt gcccattgat ctcaagggtt     1320
tacggtgaag tttgtccata tgtatctatc tccacgggat gttcaaagca tagattgtgt     1380
acttgtcttt aatagggata ttgtgtactt gtgttaatag tggaaaagtt tgattttatg     1440
ttgtacccaa agtctgaatt tttctctagt ttctatggga attttactct tgtcacgaa      1500 ctccatttaa aatttctatt tctaaacggg cttcgatggt ttgtgaagct tgcatgagtt     1560
catatttaa                                                             1569
```